United States Patent [19]

Armitage et al.

[11] Patent Number: 5,780,482
[45] Date of Patent: Jul. 14, 1998

[54] CONDENSED 4-AMINOPYRIDINES WITH ANTIRHEUMATIC ACTIVITY

[75] Inventors: Bernard John Armitage; Bruce William Leslie; Thomas Kerr Miller; Christopher Morley, all of Nottingham, Great Britain

[73] Assignee: Knoll Aktiengesellschaft, Ludwigshafen, Germany

[21] Appl. No.: 564,154

[22] PCT Filed: Jun. 10, 1994

[86] PCT No.: PCT/EP94/01923

§ 371 Date: Dec. 21, 1995

§ 102(e) Date: Dec. 21, 1995

[87] PCT Pub. No.: WO95/00511

PCT Pub. Date: Jan. 5, 1995

[30] Foreign Application Priority Data

Jun. 22, 1993 [GB] United Kingdom .................. 9312891

[51] Int. Cl.⁶ .................. A61K 31/435; C07D 471/04
[52] U.S. Cl. .................. 514/300; 546/122; 544/350; 514/303
[58] Field of Search ................. 546/122; 514/300

[56] References Cited

FOREIGN PATENT DOCUMENTS

| | | |
|---|---|---|
| 181 568 | 5/1986 | European Pat. Off. . |
| 302 303 | 2/1989 | European Pat. Off. . |
| 361 177 | 4/1990 | European Pat. Off. . |
| 410 762 | 1/1991 | European Pat. Off. . |
| 452 873 | 10/1991 | European Pat. Off. . |
| 5234 | 6/1993 | Indonesia . |
| 47-29519 | 8/1972 | Japan . |
| 63068568 | 9/1986 | Japan . |
| 84/00489 | 2/1984 | WIPO . |
| 86/06718 | 11/1986 | WIPO . |
| 90/14338 | 11/1990 | WIPO . |
| 93/13097 | 7/1993 | WIPO . |

OTHER PUBLICATIONS

Barlin et al., *Aust. J. Chem.*, vol. 37, 1984, pp. 1065–1073.
*Arch. Pharm.*, vol. 324, No. 9, 600, 1991.
Sofia et al., *Pharm. Res. Comm.*, vol. 11, No. 2, 1979.
Kuroda et al., *J. Med. Chem.*, 1992, vol. 35, pp. 1130–1136.

*Primary Examiner*—Matthew V. Grumbling
*Attorney, Agent, or Firm*—Keil & Weinkauf

[57] ABSTRACT

Compounds of formula I

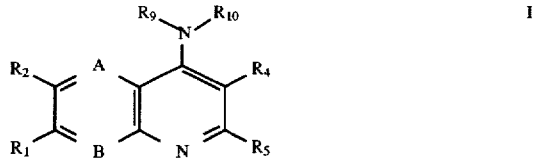

and pharmaceutically acceptable salts thereof in which one of A or B represents N and the other represents N or C—$R_3$; $R_1$ represents hydrogen, halo, alkyl, hydroxy, carboxyalkenyl, alkoxycarbonylalkenyl, hydroxyalkyl, carboxyalkyl, alkoxycarbonylalkyl, alkoxy, halogenated alkyl, carboxy, alkoxycarbonyl, alkanoylamino or carbamoylalkenyl; $R_2$ represents hydrogen, alkyl, halo, alkoxy, hydroxy, alkanoyloxy, or phenoxy; $R_3$ represents hydrogen or alkyl; $R_4$ represents hydrogen, halo, alkoxycarbonyl, cyano, benzyloxycarbonyl, alkanoyl, benzoyl, alkyl, carboxy, alkylthio or carbamoyl; $R_5$ represents hydrogen or alkyl; $R_9$ represents hydrogen or alkyl; $R_{10}$ represents phenyl, pyridyl or pyrimidinyl substituted by $OR_6$ and optionally further substituted wherein $R_6$ represents hydrogen, alkyl, alkoxycarbonyl or carbamoyl, alicyclic hydrocarbon, phenyl, cycloalkylalkyl, arylalkyl or pyridyl; or when $R_{10}$ represents phenyl, $OR_6$ represents a monosaccharide group or a disaccharide group; which are antirheumatic agents. Compositions containing these compounds and processes to prepare them are also disclosed.

14 Claims, No Drawings

CONDENSED 4-AMINOPYRIDINES WITH ANTIRHEUMATIC ACTIVITY

This is a national stage application filed under 35 U.S.C. §371 of PCT/EP94/01923, filed Jun. 10, 1994.

The present invention relates to therapeutic agents, and in particular to substituted ring-fused 4-aminopyridines, to processes for their preparation, to pharmaceutical compositions containing them and to their therapeutic activity as anti-rheumatic agents.

Rheumatoid arthritis is currently treated with anti-inflammatory agents, which alleviate the symptoms but do not affect the progression of the condition, or with disease-modifying antirheumatic drugs e.g. gold compounds, D-penicillamine, sulphasalazine, azathioprine and methotrexate. However, most disease-modifying antirheumatic drugs are associated with side-effects, often of a serious nature. This means that such drugs are often only used as a last resort in the most serious cases. Consequently a need exists for a less toxic, disease-modifying, antirheumatic drug which may be administered orally.

EP 0.361.177 discloses compounds of formula A

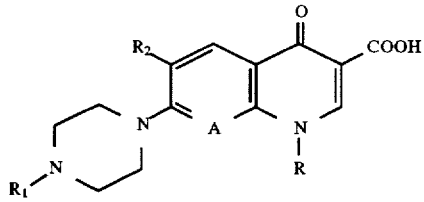

in which R represents alkyl, cyclopropyl, methylamino and p-fluorophenyl; $R_1$ represents hydrogen or a $C_{1-2}$ alkyl group; $R_2$ represents halo and A represents —CH— or —N—. It is disclosed that these compounds may be used to treat rheumatoid arthritis by intra-articular administration.

Japanese patent application number 38774/69, publication number J47-29519 (1972) discloses ethyl 4-anilino-7-methyl-1,8-naphthyridine-3-carboxylate amongst a number of compounds which are prepared as intermediates for use in the preparation of anti-bacterial agents. It is suggested that these intermediates possess anti-bacterial and antiprotozoal activity but no results are given.

2-Diethylaminomethyl-4-(7'-methyl-1',8'-naphthyridin-4'-ylamino)phenol and 2-diethylaminomethyl-4-(1',8'-naphthyridin-4-ylamino)phenol are disclosed in the Australian Journal of Chemistry, 1984, 37, 1065 as having minimal antimalarial activity.

WO 86/06718 discloses compounds of formula B

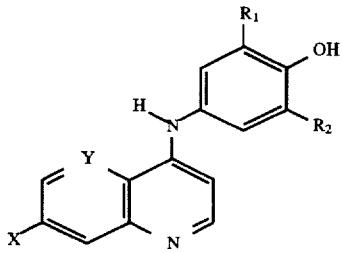

in which X represents halo or haloalkyl; Y represents —CH— or —N—; and $R_1$, $R_2$ represent hydrogen or various substituted aminoalkyl substituents in which $R_1$ and $R_2$ are not both hydrogen. The compounds are claimed to have antimalarial activity. Certain compounds of formula B in which $R_1$ and $R_2$ are both hydrogen are disclosed as intermediates.

Our co-pending application PCT/EP92/02901 (WO 93/13097) discloses compounds of formula C

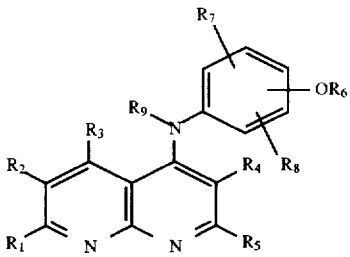

All compounds disclosed in that application are disclaimed from this present application.

The present invention relates to compounds of formula I

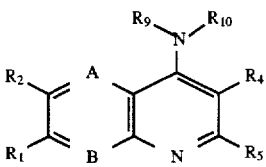

and pharmaceutically acceptable salts thereof in which one of A or B represents N and the other represents N or C—$R_3$;

$R_1$ represents hydrogen, halo, a $C_{1-6}$ alkyl group, hydroxy, a carboxy $C_{2-4}$ alkenyl group, a $C_{2-6}$ alkoxycarbonyl $C_{2-4}$ alkenyl group, a hydroxy $C_{1-6}$ alkyl group, a carboxy $C_{1-4}$ alkyl group, a $C_{2-6}$ alkoxycarbonyl $C_{1-4}$ alkyl group, a $C_{1-6}$ alkoxy group, a halogenated $C_{1-6}$ alkyl group, a carboxy group, a $C_{2-6}$ alkoxycarbonyl group, a $C_{1-6}$ alkanoylamino group or a carbamoyl $C_{2-4}$ alkenyl group;

$R_2$ represents hydrogen, a $C_{1-6}$ alkyl group, halo, a $C_{1-6}$ alkoxy group, hydroxy, a $C_{1-6}$ alkanoyloxy group (which may be substituted by a $C_{1-6}$ alkanoyloxy group), or a phenoxy group (optionally substituted by a $C_{1-4}$ alkyl group, halo or a $C_{1-4}$ alkoxy group);

$R_3$ represents hydrogen or a $C_{1-4}$ alkyl group;

$R_4$ represents hydrogen, halo, a $C_{2-7}$ alkoxycarbonyl group, cyano, a benzyloxycarbonyl group (optionally substituted by a $C_{1-4}$ alkyl group, halo or a $C_{1-4}$ alkoxy group), a $C_{1-6}$ alkanoyl group, a benzoyl group (optionally substituted by a $C_{1-4}$ alkyl group, halo or a $C_{1-4}$ alkoxy group), a $C_{1-6}$ alkyl group [optionally substituted by one or more hydroxy groups and or an amino group of formula —$NR_xR_y$ (in which $R_x$ and $R_y$ independently represent hydrogen or a $C_{1-4}$ alkyl group or $R_x$ and $R_y$ together with the nitrogen atom to which they are attached form a pyrrolidine ring, a morpholine ring or a piperidine ring)], a carboxy group, a $C_{1-6}$ alkylthio group or a carbamoyl group of formula —$CONR_aR_b$ [in which $R_a$ and $R_b$ independently represent hydrogen, a $C_{1-6}$ alkyl group (optionally substituted by an amino group of formula —$NR_cR_d$ in which $R_c$ and $R_d$ independently represent hydrogen or a $C_{1-4}$ alkyl group or $R_c$ and $R_d$ together with the nitrogen atom to which they are attached form a pyrrolidine ring, a morpholine ring or a piperidine ring) or $R_a$ and $R_b$ together with the nitrogen atom to which they are attached form a pyrrolidine ring, a morpholine ring or a piperidine ring];

$R_5$ represents hydrogen or a $C_{1-4}$ alkyl group;

$R_9$ represents hydrogen or a $C_{1-4}$ alkyl group;

$R_{10}$ represents a group of formula 1, 2 or 3:

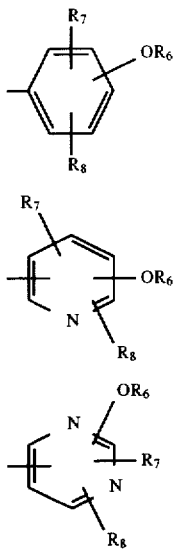

in which $R_6$ represents hydrogen, a $C_{1-6}$ alkyl group [optionally substituted by one or more of the following: hydroxy, halo, an amino group of formula—$NR_{12}R_{13}$ (in which $R_{12}$ and $R_{13}$ independently represent hydrogen or a $C_{1-4}$ alkyl group or $R_{12}$ and $R_{13}$ together with the nitrogen atom to which they are attached form a pyrrolidine ring, a morpholine ring or a piperidine ring), a $C_{2-7}$ alkoxycarbonyl group or a carbamoyl group of formula $CONR_{14}R_{15}$ (in which $R_{14}$ and $R_{15}$ independently represent hydrogen or a $C_{1-6}$ alkyl group or $R_{14}$ and $R_{15}$ together with the nitrogen to which they are attached form a pyrrolidine ring, a morpholine ring or piperidine ring)]; a $C_{3-12}$ alicyclic hydrocarbon group, a phenyl group (optionally substituted by a $C_{1-4}$ alkyl group, halo or a $C_{1-4}$ alkoxy group), a $C_{3-6}$ cycloalkyl $C_{1-4}$ alkyl group or an arylalkyl group (optionally substituted by a $C_{1-4}$ alkyl group, halo or a $C_{1-4}$ alkoxy group); a pyridyl group (optionally substituted by one or more of the following: a $C_{1-4}$ alkyl group, a $C_{1-4}$ alkoxy group, hydroxy or halo);

or when $R_{10}$ represents a group of formula (1) $OR_6$ represents a monosaccharide group or a disaccharide group (optionally derivatised by one or more of the following: oxidation; oxidation followed by esterification; esterification or acetalisation); and $R_7$ and $R_8$ independently represent hydrogen, hydroxy, halo, trifluoromethyl, trifluoromethoxy, a $C_{1-6}$ alkyl group, a carboxy group, a $C_{1-6}$ alkoxy group, or a $C_{2-7}$ alkoxycarbonyl group;

with a first proviso that when $R_1$ represents hydrogen, a $C_{1-6}$ alkyl group, hydroxy, a carboxy $C_{2-4}$ alkenyl group, a $C_{2-6}$ alkoxycarbonyl $C_{2-4}$ alkenyl group, a hydroxy $C_{1-6}$ alkyl group, a carboxy $C_{1-4}$ alkyl group, a $C_{2-6}$ alkoxycarbonyl $C_{1-4}$ alkyl group, a $C_{1-6}$ alkoxy group, a halogenated $C_{1-6}$ alkyl group, a carboxy group, a $C_{2-6}$ alkoxycarbonyl group or a $C_{1-6}$ alkanoylamino group; and $R_2$ represents hydrogen, halo, a $C_{1-6}$ alkoxy group, hydroxy, a $C_{1-6}$ alkanoyloxy group, or a phenoxy group (optionally substituted by a $C_{1-4}$ alkyl group, halo or a $C_{1-4}$ alkoxy group); and $R_4$ represents hydrogen, halo, a $C_{2-7}$ alkoxycarbonyl group, a benzyloxycarbonyl group (optionally substituted by a $C_{1-4}$ alkyl group, halo or a $C_{1-4}$ alkoxy group), a $C_{1-6}$ alkanoyl group, a benzoyl group (optionally substituted by a $C_{1-4}$ alkyl group, halo or a $C_{1-4}$ alkoxy group), carbamoyl, a $C_{1-6}$ alkyl group, a carboxy group, a $C_{1-6}$ hydroxyalkyl group or a $C_{1-6}$ alkylthio group; and $R_5$ represents hydrogen or a $C_{1-4}$ alkyl group; and $R_{10}$ represents a group of formula (1)

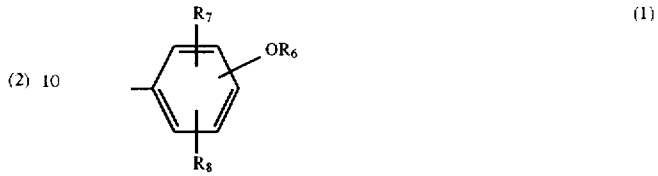

in which $R_6$ represents hydrogen, a $C_{1-6}$ alkyl group [optionally substituted by one or more of the following: hydroxy, halo or an amino group of formula—$NR_{12}R_{13}$ (in which $R_{12}$ and $R_{13}$ independently represent hydrogen or a $C_{1-4}$ alkyl group or $R_{12}$ and $R_{13}$ together with the nitrogen atom to which they are attached form a pyrrolidine ring, a morpholine ring or a piperidine ring)], a $C_{3-12}$ alicyclic hydrocarbon group, a phenyl group (optionally substituted by a $C_{1-4}$ alkyl group, halo or a $C_{1-4}$ alkoxy group), a $C_{3-6}$ cycloalkyl $C_{1-4}$ alkyl group or a benzyl group (optionally substituted by a $C_{1-4}$ alkyl group, halo or a $C_{1-4}$ alkoxy group); and $R_7$ represents hydrogen, halo, trifluoromethyl, trifluoromethoxy, a $C_{1-6}$ alkyl group, a carboxy group, or a $C_{1-6}$ alkoxy group; and $R_8$ represents hydrogen, halo, trifluoromethyl, trifluoromethoxy, a $C_{1-6}$ alkyl group or a $C_{1-6}$ alkoxy group; and $R_9$ represents hydrogen or a $C_{1-4}$ alkyl group and B represents N then A is other than $CR_3$ in which $R_3$ represents hydrogen or a $C_{1-4}$ alkyl group and a second proviso that when A represents N and B represents CH; $R_1$ represents halo or a halogenated $C_{1-6}$ alkyl group; and $R_2$, $R_4$, $R_5$ and $R_9$ each represent hydrogen then $R_{10}$ is other than 4-hydroxyphenyl.

It will be understood that an alkyl group containing 3 or more carbon atoms may be straight or branched, for example, propyl includes n-propyl and isopropyl and butyl includes n-butyl, sec-butyl, isobutyl and tert-butyl. Alicyclic groups may be bridged.

In the present invention the phrase "a monosaccharide group or a disaccharide group (optionally derivatised by one or more of the following: oxidation; oxidation followed by esterification; esterification or acetalisation);" is used to indicate that the monosaccharide or disaccharide has been derivatised in one of the following ways. Firstly, the 6-position of the saccharide may be oxidised to give the corresponding 6-carboxylic acid e.g. glucose may be oxidised to give glucuronic acid or a hydroxyl group on the saccharide may be oxidised to give a keto-sugar. Secondly, a carboxylic acid produced by oxidation may be esterified by methods known to those skilled in the art. Thirdly, a free hydroxy group on the saccharide may be esterified by treatment with an organic acid or an organic acid derivative. Fourthly, hydroxy groups on adjacent carbon atoms of the saccharide may be reacted with an aldehyde or a ketone to give an acetal or a ketal.

A preferred group of compounds of formula I is represented by formula IIa

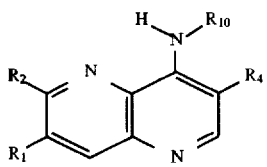

in which $R_1$ represents hydrogen, halo, a $C_{1-6}$ alkyl group, hydroxy, a carboxy $C_{2-4}$ alkenyl group, a $C_{2-6}$ alkoxycarbonyl $C_{2-4}$ alkenyl group, a hydroxy $C_{1-6}$ alkyl group, a carboxy $C_{1-4}$ alkyl group, a $C_{2-6}$ alkoxycarbonyl $C_{1-4}$ alkyl group, a $C_{1-6}$ alkoxy group, a halogenated $C_{1-6}$ alkyl group, a carboxy group, a $C_{2-6}$ alkoxycarbonyl group, a $C_{1-6}$ alkanoylamino group or a carbamoyl $C_{2-4}$ alkenyl group;

$R_2$ represents hydrogen, a $C_{1-6}$ alkyl group, halo, a $C_{1-6}$ alkoxy group, a $C_{1-6}$ alkyl group, a $C_{1-6}$ alkoxy group, hydroxy, a $C_{1-6}$ alkanoyloxy group (which may be substituted by a $C_{1-6}$ alkanoyloxy group), or a phenoxy group (optionally substituted by a $C_{1-4}$ alkyl group, halo or a $C_{1-4}$ alkoxy group);

$R_4$ represents hydrogen, carbamoyl, a $C_{2-7}$ alkoxycarbonyl group or cyano; and $R_{10}$ represents a group of formula 1, 2 or 3:

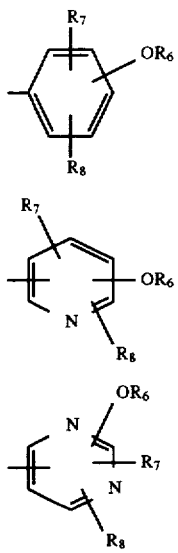

(1)

(2)

(3)

in which $R_6$ represents hydrogen, a $C_{1-6}$ alkyl group [optionally substituted by one or more of the following: hydroxy, halo, an amino group of formula—$NR_{12}R_{13}$ (in which $R_{12}$ and $R_{13}$ independently represent hydrogen or a $C_{1-4}$ alkyl group or $R_{12}$ and $R_{13}$ together with the nitrogen atom to which they are attached form a pyrrolidine ring, a morpholine ring or a piperidine ring), a $C_{2-7}$ alkoxycarbonyl group or a carbamoyl group of formula $CONR_{14}R_{15}$ (in which $R_{14}$ and $R_{15}$ independently represent hydrogen or a $C_{1-6}$ alkyl group or $R_{14}$ and $R_{15}$ together with the nitrogen atom to which they are attached form a pyrrolidine ring, a morpholine ring or piperidine ring)], a $C_{3-12}$ alicyclic hydrocarbon group, a phenyl group (optionally substituted by a $C_{1-4}$ alkyl group, halo or a $C_{1-4}$ alkoxy group), a $C_{3-6}$ cycloalkyl $C_{1-4}$ alkyl group or an arylalkyl group (optionally substituted by a $C_{1-4}$ alkyl group, halo or a $C_{1-4}$ alkoxy group), or a pyridyl group (optionally substituted by one or more of the following: a $C_{1-4}$ alkyl group, a $C_{1-4}$ alkoxy group, hydroxy or halo); or when $R_{10}$ represents a group of formula (1) $OR_6$ represents a monosaccharide group or a disaccharide group (optionally derivatised by one or more of the following: oxidation; oxidation followed by esterification; esterification or acetalisation); and $R_7$ and $R_8$ independently represent hydrogen, hydroxy, halo, trifluoromethyl, trifluoromethoxy, a $C_{1-6}$ alkyl group, a carboxy group, a $C_{1-6}$ alkoxy group, or a $C_{2-7}$ alkoxycarbonyl group.

In preferred compounds of formula IIa the preferred values for groups $R_1$, $R_2$, $R_4$ and $R_{10}$ are listed below.

Preferably $R_1$ represents hydrogen or chloro. More preferably $R_1$ represents hydrogen.

Preferably $R_2$ represents hydrogen, a $C_{1-4}$ alkyl group, a $C_{1-4}$ alkoxy group (for example methoxy, ethoxy, propoxy or butoxy), or phenoxy. More preferably $R_2$ represents hydrogen, ethyl, ethoxy, or phenoxy. Most preferably $R_2$ represents ethoxy.

Preferably $R_4$ represents hydrogen or a $C_{2-5}$ alkoxycarbonyl group (for example methoxycarbonyl, ethoxycarbonyl, propoxycarbonyl or butoxycarbonyl). More preferably $R_4$ represents a $C_{2-4}$ alkoxycarbonyl group. Most preferably $R_4$ represents ethoxycarbonyl.

More preferably $R_{10}$ represents 4-methoxyphenyl, 4-(2-pyridyloxyphenyl), 2-ethoxy-5-pyridyl, 4-(2-hydroxyethoxy)phenyl, |4-($\beta$-D-galactopyranosyl)phenyl, 4-(2,3-dihydroxypropoxy)phenyl or 3-ethoxycarbonyl-4-hydroxyphenyl. Most preferably $R_{10}$ represents 4-methoxyphenyl.

A second preferred group of compounds of formula I is represented by formula IIb

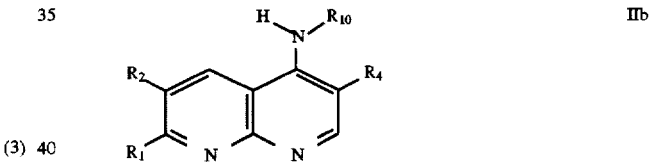

in which $R_1$ represents hydrogen, a $C_{1-4}$ alkyl group, a $C_{1-4}$ alkoxy group or a carbamoyl $C_{2-4}$ alkenyl group;

$R_2$ represents hydrogen, a $C_{1-4}$ alkoxy group or acetoxyacetoxy;

$R_4$ represents hydrogen, a $C_{2-7}$ alkoxycarbonyl group, cyano or carbamoyl;

$R_{10}$ represents a group of formula 1, 2 or 3:

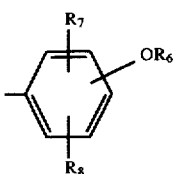

(1)

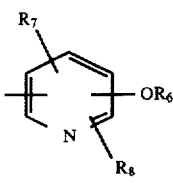

(2)

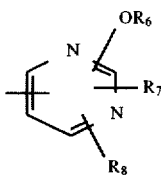

(3)

in which $R_6$ represents hydrogen, a $C_{1-6}$ alkyl group [optionally substituted by one or more of the following: hydroxy, halo, an amino group of formula—$NR_{12}R_{13}$ (in which $R_{12}$ and $R_{13}$ independently represent hydrogen or a $C_{1-4}$ alkyl group or $R_{12}$ and $R_{13}$ together with the nitrogen atom to which they are attached form a pyrrolidine ring, a morpholine ring or a piperidine ring), a $C_{2-7}$ alkoxycarbonyl group or a carbamoyl group of formula $CONR_{14}R_{15}$ (in which $R_{14}$ and $R_{15}$ independently represent hydrogen or a $C_{1-6}$ alkyl group or $R_{14}$ and $R_{15}$ together with the nitrogen to which they are attached form a pyrrolidine ring, a morpholine ring or piperidine ring)]; a $C_{3-12}$ alicyclic hydrocarbon group, a phenyl group (optionally substituted by a $C_{1-4}$ alkyl group, halo or a $C_{1-4}$ alkoxy group), a $C_{3-6}$ cycloalkyl $C_{1-4}$ alkyl group or an arylalkyl group (optionally substituted by a $C_{1-4}$ alkyl group, halo or a $C_{1-4}$ alkoxy group); a pyridyl group (optionally substituted by one or more of the following: a $C_{1-4}$ alkyl group, a $C_{1-4}$ alkoxy group, hydroxy or halo);

or when $R_{10}$ represents a group of formula (1) $OR_6$ represents a monosaccharide group or a disaccharide group (optionally derivatised by one or more of the following: oxidation; oxidation followed by esterification; esterification or acetalisation); and $R_7$ and $R_8$ independently represent hydrogen, hydroxy, halo, trifluoromethyl, trifluoromethoxy, a $C_{1-6}$ alkyl group, a carboxy group, a $C_{1-6}$ alkoxy group, or a $C_{2-7}$ alkoxycarbonyl group.

In preferred compounds of formula IIb the preferred values of $R_1$, $R_2$, $R_4$ and $R_{10}$ are listed below.

Preferably $R_1$ represents hydrogen, a $C_{1-3}$ alkyl group or a $C_{1-3}$ alkoxy group. More preferably $R_1$ represents hydrogen, methyl, ethyl or ethoxy. Most preferably $R_1$ represents methyl.

Preferably $R_2$ represents a $C_{1-4}$ alkoxy group. More preferably $R_2$ represents ethoxy or propoxy. Most preferably $R_2$ represents ethoxy.

Preferably $R_4$ represents cyano, carbamoyl or a $C_{2-5}$ alkoxycarbonyl group. More preferably $R_4$ represents a $C_{2-5}$ alkoxycarbonyl group. More preferably $R_4$ represents ethoxycarbonyl.

Preferably $R_{10}$ represents 4-methoxyphenyl, 6-ethoxy-3-pyridyl, 6-hydroxy-3-pyridyl, 6-ethoxy-2-pyridyl, 4-(carbamoylmethoxy)phenyl, 2,4-dihydroxy-5-pyrimidinyl, 2-(pyrid-3-yloxy)pyrid-5-yl, 2-phenoxy-5-pyridyl, 4-(ethoxycarbonylmethoxy)phenyl, 3-ethoxycarbonyl-4-hydroxyphenyl, 4-(2-pyridyloxy)phenyl, 4-(β-D-lactopyranosyl)phenyl or 4-(β-D-galactopyranosyl)phenyl.

A third group of preferred compounds of formula I is represented by formula IIc

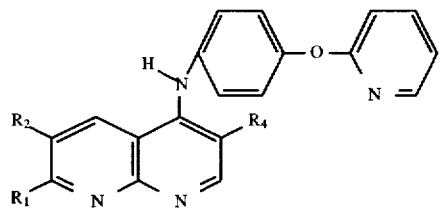

in which $R_1$ represents hydrogen, a $C_{1-4}$ alkyl group or a $C_{1-4}$ alkoxy group;

$R_2$ represents hydrogen or $C_{1-4}$ alkoxy group; and $R_4$ represents hydrogen or a $C_{2-5}$ alkoxycarbonyl group.

A preferred group of compounds of formula IIc is now given.

Preferably $R_1$ represents hydrogen or a $C_{1-4}$ alkyl group. More preferably $R_1$ represents methyl.

Preferably $R_2$ represents hydrogen, methoxy, ethoxy or propoxy. More preferably $R_2$ represents ethoxy.

Preferably $R_4$ represents hydrogen, methoxycarbonyl, ethoxycarbonyl or propoxycarbonyl. More preferably $R_4$ represents ethoxycarbonyl.

A fourth group of preferred compounds of formula I is represented by formula IId

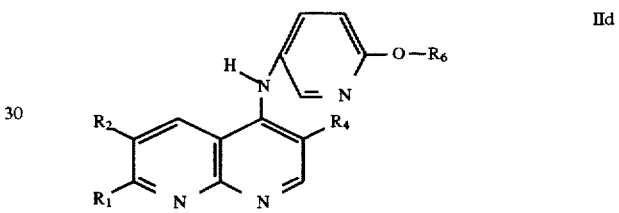

in which $R_1$ represents hydrogen, a $C_{1-4}$ alkyl group or a $C_{1-4}$ alkoxy group;

$R_2$ represents hydrogen or a $C_{1-4}$ alkoxy group;

$R_4$ represents hydrogen or a $C_{2-5}$ alkoxycarbonyl group and $R_6$ represents hydrogen or a $C_{1-4}$ alkyl group.

A preferred group of compounds of formula IId is now given.

Preferably $R_1$ represents hydrogen, methyl, ethyl or ethoxy. More preferably $R_1$ represents methyl.

Preferably $R_2$ represents hydrogen, methoxy, ethoxy or propoxy. More preferably $R_2$ represents ethoxy.

Preferably $R_4$ represents hydrogen, methoxycarbonyl, ethoxycarbonyl or propoxycarbonyl. More preferably $R_4$ represents hydrogen or ethoxycarbonyl.

Preferably $R_6$ represents hydrogen, methyl, ethyl or propyl. More preferably $R_6$ represents ethyl.

Specific compounds of formula I are:

ethyl 6-ethoxy-4-(4-methoxyanilino)-1,5-naphthyridine-3-carboxylate ethyl 6-ethoxy-4-[4-(2-diethylaminoethoxy)anilino]-1,5-naphthyridine-3-carboxylate ethyl 6-methoxy-4-(4-methoxyanilino)-1,5-naphthyridine-3-carboxylate ethyl 6-ethoxy-4-[4-(2-pyridyloxy)anilino]-1,5-naphthyridine-3-carboxylate ethyl 6-ethoxy-4-(2-ethoxy-5-pyridylamino)-1,5-naphthyridine-3-carboxylate ethyl 6-ethoxy-4-[4-(2-hydroxyethoxy)anilino]-1,5-naphthyridine-3-carboxylate ethyl 6-ethoxy-4-[4-(β-D-galactopyranosyl)anilino]-1,5-naphthyridine-3-carboxylate ethyl 4-(4-methoxyanilino)-6-phenoxy-1,5-naphthyridine-3-carboxylate hydrochloride 7-chloro-4-(4-methoxyanilino)-1,5-naphthyridine ethyl 6-ethyl-4-(4-methoxyanilino)-1,5-naphthyridine-3-carboxylate ethyl 6-ethoxy-4-[4-(2,3-dihydroxypropoxy)anilino]-1,5-naphthyridine-3-carboxylate ethyl 3-ethoxy-8-(4-methoxyanilino)-pyrido[2,3-b]pyrazine-7-carboxylate ethyl 5-(6-ethoxy-3-ethoxycarbonyl-1,5-naphthyridin-4-ylamino) salicylate 5-(4-methoxyanilino)-2-methyl-1,8-naphthyridin-3-yl acetoxyacetate ethyl 7-(2-carbamoylvinyl)-6-ethoxy-4-(4-methoxyanilino)-1,8-naphthyridine-3-carboxylate ethyl 6-ethoxy-4-(2-ethoxy-5-pyridylamino)-7-methyl-1,8-naphthyridine-3-carboxylate 5-(3-ethoxy-2-methyl-1,8-naphthyridin-5-ylamino)pyridin-2-ol 3-ethoxy-5-(2-ethoxy-5-pyridylamino)-2-methyl-1,8-naphthyridine ethyl 7-ethoxy-4-(2-ethoxy-5-pyridylamino)-1,8-naphthyridine-3-carboxylate 3-ethoxy-5-(6-ethoxy-2-pyridylamino)-2-methyl-1,8-naphthyridine ethyl 6-ethoxy-4-(6-ethoxy-2-pyridylamino)-7-methyl-1,8-naphthyridine-3-carboxylate 6-ethoxy-4-(4-methoxyanilino)-7-methyl-1,8-naphthyridine-3-carbonitrile ethyl 4-[4-(carbamoylmethoxy)anilino]-6-ethoxy-7-methyl-1,8-naphthyridine-3-carboxylate ethyl 4-(2,4-dihydroxy-5-pyrimidinylamino)-6-ethoxy-7-methyl-1,8-naphthyridine-3-carboxylate 2-methyl-5-[2-(pyrid-3-yloxy)pyrid-5-ylamino]-1,8-naphthyridine ethyl 6-ethoxy-7-methyl-4-(2-phenoxy-5-pyridylamino)-1,8-naphthyridine-3-carboxylate ethyl 4-(6-ethoxy-3-ethoxycarbonyl-7-methyl-1,8-naphthyridin-4-ylamino)phenoxyacetate ethyl 5-(6-ethoxy-3-ethoxycarbonyl-7-methyl-1,8-naphthyridin-4-ylamino)salicylate 3-O-[4-(6-ethoxy-3-ethoxycarbonyl-7-methyl-1,8-naphthyridin-4-ylamino)phenyl]-1,2-O-isopropylidene-glucofuranose ethyl 6-ethoxy-4-[4-(β-D-galactopyranosyl)anilino]-7-methyl-1,8-naphthyridine-3-carboxylate 4-(6-ethoxy-7-methyl-1,8-naphthyridin-4-ylamino)phenyl β-D-galactopyranoside 3-O-[4-(6-ethoxy-7-methyl-1,8-naphthyridin-4-ylamino)phenyl]-1,2:5,6-di-O-isopropylidene-D-glucofuranose ethyl 6-ethoxy-4-[4-(β-D-lactopyranosyl)anilino]-7-methyl-1,8-naphthyridine-3-carboxylate 6-ethoxy-4-[4-(β-D-lactopyranosyl)anilino]-7-methyl-1,8-naphthyridine-3-carboxamide ethyl 4-[4-(β-D-galactopyranosyl)anilino]-7-methyl-6-propoxy-1,8-naphthyridine-3-carboxylate 2-methyl-5-[4-(2-pyridyloxy)anilino]-1,8-naphthyridine ethyl 7-methyl-4[4-(2-pyridyloxy)-anilino]-1,8-naphthyridine-3-carboxylate ethyl 6-ethoxy-7-methyl-4-[4-(2-pyridyloxy)anilino]-1,8-naphthyridine-3-carboxylate 3-ethoxy-2-methyl-5-[4-(2-pyridyloxy)anilino]-1,8-naphthyridine methyl [4-(6-ethoxy-3-ethoxycarbonyl-7-methyl-1,8-naphthyridin-4-ylamino)phenyl-2,3,4-tri-O-acetyl-β-D-glucopyranosid]uronate ethyl 4-(4-hydroxyanilino)-6-methoxy-1,5-naphthyridine-3-carboxylate 4-(6-methoxy-2-methyl-1,5-naphthyridin-4-ylamino)-2-methylphenol 4-[4-(2-butoxy)anilino]-6-methoxy-2-methyl-1,5-naphthyridine and pharmaceutically acceptable salts thereof, in the form of individual enantiomers, racemates or other mixtures of enantiomers.

When a compound of formula I contains a single chiral centre it may exist in two enantiomeric forms. The present invention includes individual enantiomers and mixtures of those enantiomers. The enantiomers may be obtained by methods known to those skilled in the art. Such methods typically include resolution via formation of diastereoisomeric salts or complexes which may be separated, for example, by crystallisation; resolution via formation of diastereoisomeric derivatives or complexes which may be separated, for example, by crystallisation, gas-liquid or liquid chromatography; selective reaction of one enantiomer by reaction with an enantiomer-specific reagent, for example, enzymatic esterification, oxidation or reduction, followed by separation of the modified and unmodified enantiomers; or gas-liquid or liquid chromatography in a chiral environment, for example on a chiral support such as silica with a bound chiral ligand or in the presence of a chiral solvent. It will be appreciated that where the desired enantiomer is converted into another chemical entity by one of the separation processes described above, a further step will subsequently be required to liberate the desired enantiomeric form. Alternatively, specific enantiomers may be synthesised by asymmetric synthesis using optically active reagents, substrates, catalysts or solvents, or by converting one enantiomer into the other by asymmetric transformation.

When a compound of formula I contains more than one chiral centre it may exist in diastereoisomeric forms. The diastereoisomeric pairs may be separated by methods known to those skilled in the art, for example, chromatography or crystallisation and the individual enantiomers within each pair may be separated as described above. The present invention includes each diastereoisomer of compounds of formula I or II and mixtures thereof.

Certain compounds of formula I may exist in different tautomeric forms which fall within the scope of the present invention.

Some compounds of formula I may exist in the form of solvates, for example, hydrates, which also fall within the scope of the present invention.

The compounds of formula I may form organic or inorganic salts, for example, the compounds of formula I may form acid addition salts with inorganic or organic acids, e.g. hydrochloric acid, hydrobromic acid, fumaric acid, tartaric acid, citric acid, sulphuric acid, hydriodic acid, maleic acid, acetic acid, succinic acid, benzoic acid, pamoic acid, palmitic acid, dodecanoic acid and acidic amino acids such as glutamic acid. Some compounds of formula I may form base addition salts, for example, with alkali metals for example sodium hydroxide, or with aminoacids for example, lysine or arginine. It will be appreciated that such salts, provided they are pharmaceutically acceptable may be used in therapy in place of the corresponding compounds of formula I. Such salts are prepared by reacting the compound of formula I with a suitable acid or base in a conventional manner. Such salts may also exist in form of solvates (for example, hydrates).

Certain compounds of formula I may exist in more than one crystal form and the present invention includes each crystal form and mixtures thereof.

The present invention also provides pharmaceutical compositions containing a therapeutically effective amount of a compound of formula I (including the compounds of the second proviso) together with a pharmaceutically acceptable diluent or carrier. Such pharmaceutical formulations may be used in the treatment of rheumatic diseases for example rheumatoid arthritis or osteoarthritis.

As used hereinafter, the term "active compound" denotes a compound of formula I. In therapeutic use, the active compound may be administered orally, rectally, parenterally, topically, ocularly, aurally, nasally, intravaginally or to the buccal cavity, to give a local and/or systemic effect. Thus the therapeutic compositions of the present invention may take the form of any of the known pharmaceutical compositions for such methods of administration. The compositions may be formulated in a manner known to those skilled in the art so as to give a controlled release, for example rapid release or sustained release, of the compounds of the present invention. Pharmaceutically acceptable carriers suitable for use in such compositions are well known in the art of pharmacy. The compositions of the invention may contain 0.1–99% by weight of active compound. The compositions of the invention are generally prepared in unit dosage form. Preferably the unit dosage of active ingredient is 1–500 mg. The excipients used in the preparation of these compositions are the excipients known in the pharmacist's art.

Compositions for oral administration are preferred compositions of the invention and there are known pharmaceutical forms for such administration, for example tablets, capsules, granules, syrups and aqueous or oily suspensions.

Tablets may be prepared from a mixture of the active compound with fillers such as lactose or calcium phosphate, disintegrating agents, for example maize starch, lubricating agents, for example magnesium stearate, binders for example microcrystalline cellulose or polyvinyl pyrrolidone and other optional ingredients known in the art to permit tableting the mixture by known methods. The tablets may, if desired, be coated using known methods and excipients which may include enteric coating using for example hydroxypropylmethyl-cellulose phthalate. The tablets may be formulated in a manner known to those skilled in the art so as to give a sustained release of the compounds of the present invention. Such tablets may, if desired, be provided with enteric coatings by known methods, for example by the use of cellulose acetate phthalate.

Similarly, capsules, for example hard or soft gelatin capsules, containing the active compound with or without added excipients, may be prepared by known methods and, if desired, provided with enteric coatings in a known manner. The tablets and capsules may conveniently each contain 0.1 to 1000 mg (for example 10 mg, 50 mg, 100 mg, 200 mg, 400 mg or 800 mg) of the active compound. Other compositions for oral administration include, for example, aqueous suspensions containing the active compound in an aqueous medium in the presence of a non-toxic suspending agent such as sodium carboxymethylcellulose, and oily suspensions containing a compound of the present invention in a suitable vegetable oil, for example sunflower oil.

The active compound may be formulated into granules with or without additional excipients. The granules may be ingested directly by the patient or they may be added to a suitable liquid carrier (for example water) before ingestion. The granules may contain disintegrants (for example a pharmaceutically acceptable effervescent couple formed from an acid and a carbonate or bicarbonate salt) to facilitate dispersion in the liquid medium.

Compositions for topical administration are also preferred compositions of the invention. The pharmaceutically active compound may be dispersed in a pharmaceutically acceptable cream, ointment or gel. A suitable cream may be prepared by incorporating the active compound in a topical vehicle such as petrolatum and/or light liquid paraffin, dispersed in an aqueous medium using surfactants. An ointment may be prepared by mixing the active compound with a topical vehicle such as a mineral oil, petrolatum and/or a wax e.g. paraffin wax or beeswax. A gel may be prepared by mixing the active compound with a topical vehicle comprising a gelling agent e.g. basified Carbomer BP, in the presence of water. Topically administrable compositions may also comprise a matrix in which the pharmaceutically active compounds of the present invention are dispersed so that the compounds are held in contact with the skin in order to administer the compounds transdermally. A suitable transdermal composition may be prepared by mixing the pharmaceutically active compound with a topical vehicle, such as described above, together with a potential transdermal accelerant such as dimethyl sulphoxide or propylene glycol.

Compositions of the invention suitable for rectal administration are known pharmaceutical forms for such administration, for example suppositories with hard fat, synthetic glycerides or polyethylene glycol bases.

Compositions of the invention suitable for parenteral administration are known pharmaceutical forms for such administration, for example sterile suspensions or sterile solutions in a suitable solvent.

Compositions of the invention suitable for inhalation via the mouth and/or the nose are the known pharmaceutical forms for such administration, for example aerosols, nebulised solutions or powders. Metered dose systems, known to those skilled in the art, may be used.

Compositions suitable for application to the buccal cavity include slow dissolving tablets, troches, chewing gum, gels, pastes, powders, mouthwashes or rinses.

The compounds of the present invention may also be administered by continuous infusion either from an external source, for example by intravenous infusion, or from a source of the compound placed within the body. Internal sources include implanted reservoirs containing the compound to be infused which is continuously released for example by osmosis and implants which may be a) liquid such as an oily solution or suspension of the compound to be infused for example in the form of a very sparingly water-soluble derivative such as a dodecanoate salt or b) solid in the form of an implanted support for example of a synthetic resin of waxy material for the compound to be infused. The support may be a single body containing all the compound or a series of several bodies each containing part of the compound to be delivered.

In some formulations it may be beneficial to use the compounds of the present invention in the form of particles of very small size, for example as obtained by fluid energy milling.

In the compositions of the present invention the active compound may, if desired, be associated with other compatible pharmacologically active ingredients, for example, a non-steroidal antiinflammatory agent e.g. ibuprofen, S(+)-ibuprofen, flurbiprofen or S(+)-flurbiprofen, an analgesic or an antipyretic agent.

The compounds of formula I are indicated for use as anti-rheumatic agents by their activity demonstrated by means of tests on standard laboratory animals. Such tests include, for example, the oral administration of compounds of formula I to mice with experimental antigen-induced arthritis. Compounds of formula I are suitable for use in treating rheumatic diseases for example rheumatoid arthritis, osteoarthritis, osteoporosis, crystal arthropathies (e.g. gout), reactive arthritis, ankylosing spondylitis or psoriatic arthropathy.

Compounds of formula I may also be suitable for the treatment of diseases of the oral cavity for example periodontitis, gingivitis and alveolar bone resorption.

Accordingly, in a further aspect, the present invention also includes a method of treating rheumatic diseases, particularly rheumatoid arthritis and osteoarthritis, comprising the administration of a therapeutically effective amount of a compound of formula I (including the compounds of the second proviso) to a mammal in need thereof. Compounds of formula I may also be administered in a prophylactic manner to mammals, particularly humans who have been identified as being susceptible to arthritic diseases. Whilst the precise amount of active compound administered will depend on a number of factors, for example the age of the patient, the severity of the condition and the past medical history and always lies within the sound discretion of the administering physician, a suitable dose for oral administration to mammals, including humans, is generally within the range 0.01–80 mg/kg/day, more usually 0.2–40 mg/kg/day given in single or divided doses. For parenteral administration, a suitable dose is generally within the range 0.001–80 mg/kg/day, more usually 0.2–40 mg/kg/day given in single or divided doses or by continuous infusion. A suitable preparation for topical administration generally contains the active ingredient within the range 0.01–20% by weight, more usually 0.05–5% by weight. Oral administration is preferred.

The pharmaceutical compositions containing a therapeutically effective amount of a compound of formula I may be used to treat rheumatic diseases such as rheumatoid arthritis and osteoarthritis. In such treatment the amount of the compound of formula I administered per day is in the range 0.1 to 6000 mg.

In yet another aspect, the present invention provides the use of a compound of formula I (including the compounds of the second proviso) in the manufacture of a medicament for use in the treatment of a rheumatic disease such as rheumatoid arthritis and osteoarthritis.

Processes for the preparation of compounds of formula I will now be described. These processes form a further aspect of the present invention.

Compounds of formula I may be converted into other compounds of formula I by functional group modifications known to those skilled in the art. For example, carboxylic acids may be reacted with amines to give amides or with alcohols to give esters.

Compounds of formula I in which $R_1$ represents a carboxy $C_{2-4}$ alkyl group may be prepared by reducing a compound of formula I in which $R_1$ represents a carboxy $C_{2-4}$ alkenyl group, for example with a reducing agent, e.g. hydrogen in the presence of a catalyst e.g. palladium.

Compounds of formula I in which $R_1$ represents hydroxy may be prepared by hydrolysis of a compound of formula I in which $R_1$ represents a $C_{1-6}$ alkoxy group, for example using a base e.g. sodium hydroxide.

Compounds of formula I in which $R_4$ represents an α-hydroxy $C_{1-6}$ alkyl group may be prepared by reducing a compound of formula I in which $R_4$ represents a $C_{2-7}$ alkoxycarbonyl group or a $C_{1-6}$ alkanoyl group, by methods known to those skilled in the art, for example using lithium aluminium hydride or lithium triethylborohydride.

Compounds of formula I in which $R_2$ represents hydroxy may be prepared by reacting a compound of formula I in which $R_2$ represents a $C_{1-6}$ alkoxy group with a de-alkylating agent for example aluminium chloride.

Compounds of formula I in which $R_4$ represents carboxy may be prepared by hydrolysis of compounds of formula I in which $R_4$ represents a $C_{2-6}$ alkoxycarbonyl group by methods known to those skilled in the art, for example using an acid e.g. hydrochloric acid or a base e.g. sodium hydroxide.

Compounds of formula I in which $R_1$ represents an ω-hydroxy $C_{1-6}$ alkyl may be prepared by reducing a compound of formula I in which $R_1$ represents a $C_{2-6}$ alkoxycarbonyl group or a $C_{2-6}$ alkoxycarbonyl $C_{1-4}$ alkyl group by methods known to those skilled in the art for example using lithium aluminium hydride or lithium triethylborohydride.

Compounds of formula I in which $R_1$ represents a carboxyvinyl group may be prepared by reacting compounds of formula I in which $R_1$ represents methyl with glyoxylic acid for example by heating together optionally in the presence of a catalyst e.g. trifluoroacetic acid.

Compounds of formula I in which $R_2$ represents a substituted alkanoyloxy compound may be prepared by acylating a compound of formula I in which $R_2$ represents hydroxy by methods known to those skilled in the art.

Compounds of formula I may be prepared by reacting a compound of formula III

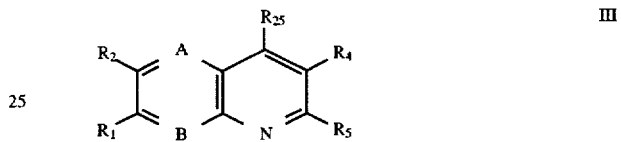

in which $R_{25}$ represents a leaving group, including halo, e.g. bromo, chloro, mercapto or methylthio with a compound of formula IV

or a salt thereof by heating, optionally in the presence of an inert organic liquid which is preferably a solvent for the reactants, e.g. an alcohol or an ether, at a temperature in the range 0°–150° C., preferably in the range 30°–120° C., at atmospheric pressure, optionally in the presence of an acid, for example hydrochloric acid, or a base, for example sodium carbonate or sodium bicarbonate.

Compounds of formula I in which $R_1$ represents a $C_{1-6}$ alkoxy group may be prepared by reacting a compound of formula XVII

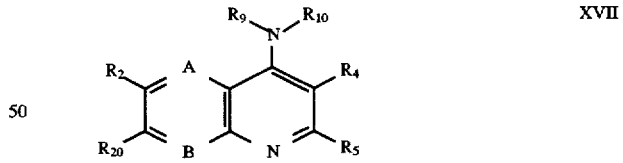

in which $R_{20}$ represents a leaving group, for example halo, with an alkali metal $C_{1-6}$ alkoxide, by heating optionally in the presence of an inert organic liquid which is preferably a solvent for the reactants, for example an alcohol, at a temperature in the range 50°–250° C. preferably 150°–200° C. preferably in a sealed vessel under pressure.

Compounds of formula I in which $R_1$ represents hydroxy may be prepared by displacing $R_{20}$ from a compound of formula XVII, in which $R_{20}$ represents a leaving group, for example halo, with a hydroxy group, for example by reacting with an alkali metal hydroxide in the presence of an inert organic liquid or by hydrolysis using an aqueous acid or base, at a temperature in the range 0°–200° C.

Compounds of formula III in which $R_{25}$ represents halo may be prepared by reacting compounds of formula V

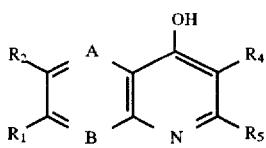

with a halogenating agent for example phosphorus oxychloride or phosphorus oxybromide at a temperature in the range 0°–150° C., preferably 20°–100° C., optionally in the presence of an inert organic liquid which is preferably a solvent for the reactants. Compounds of formula III in which $R_{25}$ represents mercapto or methylthio may be prepared from compounds of formula V by methods known to those skilled in the art.

Compounds of formula V in which $R_1$ represents hydrogen may be prepared by the thermal decarboxylation of compounds of formula VI

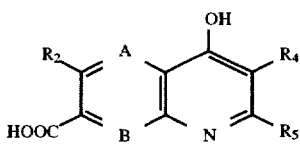

for example by heating at a temperature in the range 100°–350° C. in a suitable organic liquid e.g. diphenyl ether, quinoline or liquid petrolatum.

Compounds of formula V in which $R_1$ represents a substituent other than hydrogen may be prepared by heating compounds of formula VII

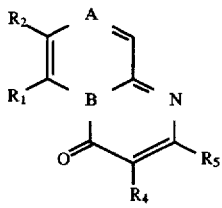

in which $R_1$ represents a substituent other than hydrogen in the presence of a suitable solvent, for example diphenyl ether or liquid petrolatum at a temperature in the range 150° to 350° C.

Compounds of formula V in which $R_4$ represents hydrogen may be prepared by heating compounds of formula V in which $R_4$ represents $COOR_{16}$ and $R_{16}$ represents hydrogen or a $C_{1-4}$ alkyl group, with aqueous sodium hydroxide solution in a sealed vessel or by thermal decarboxylation of compounds of formula V in which $R_{16}$ represents hydrogen optionally in the presence of an organic liquid, for example quinoline or liquid petrolatum.

Compounds of formula VI may be prepared by oxidising compounds of formula V in which $R_1$ represents a $C_{1-6}$ alkyl group, for example with selenium dioxide, or by oxidising compounds of formula V in which $R_1$ represents a carboxyvinyl group for example with potassium permanganate.

Compounds of formula VII may be prepared by heating compounds of formula VIII

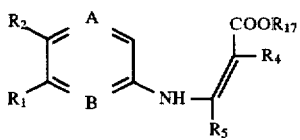

in which $R_{17}$ represents a $C_{1-4}$ alkyl group in the presence of a suitable solvent, for example diphenyl ether or liquid petrolatum at a temperature in the range 150° to 350° C., or by reacting compounds of formula VIII with phosphorus oxychloride in the presence of polyphosphoric acid.

Compounds of formula VIII, in which $R_1$ represents a substituent as defined above, other than hydrogen, may be heated in the presence of an organic liquid, for example diphenyl ether or liquid petrolatum at a temperature in the range of 150° to 350° C. to produce compounds of formula V.

Compounds of formula VIII in which $R_5$ represents hydrogen may be prepared by reacting a compound of formula IX

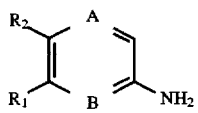

with a compound of formula X

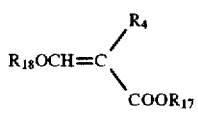

in which $R_{17}$ or $R_{18}$ independently represent a $C_{1-4}$ alkyl group or with a compound of formula XI

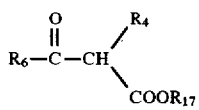

or a salt thereof, e.g. the sodium salt, in which $R_{17}$ represents a $C_{1-4}$ alkyl group, in the presence of a suitable solvent, for example ethanol, at a temperature in the range 50° to 200° C.

Compounds of formula VIII in which $R_5$ represents hydrogen may also be prepared by reacting a compound of formula IX with a tri($C_{1-4}$ alkyl)orthoformate and a compound of formula $R_4CH_2CO_2R_{17}$, for example by heating, optionally in the presence of a solvent for example acetic anhydride and/or a Lewis acid catalyst for example zinc chloride.

Compounds of formulae IX, X and XI may be prepared by methods known to those skilled in the art.

Compounds of formula XII

may be reduced for example, by heating in the presence of reduced iron powder and dilute acid or by hydrogenation in the presence of a catalyst e.g. palladium, to prepare compounds of formula IV, in which $R_9$ represents hydrogen.

Compounds of formulae XII, may be prepared by methods known to those skilled in the art.

Compounds of formula XVII may be prepared by reacting a compound of formula XVIII

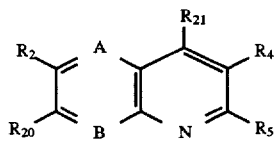

in which $R_{21}$ represents halo, for example chloro or bromo, with a compound of formula IV using conditions analogous to those described for the preparation of compounds of formula I from a compound of formula III and a compound of formula IV.

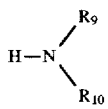

Compounds of formula XVIII may be prepared by processes analogous to those described for the preparation of compounds of formula III.

Certain intermediate compounds of formulae III–X inclusive are believed to be novel compounds. All novel compounds herein form a further aspect of the invention.

The therapeutic activity of the compounds of the present invention has been demonstrated by tests which include the oral administration of the compounds to mice with experimental antigen-induced arthritis. The compounds showed activity in the following test:

Female BALB/c mice, 8 weeks of age were used: each control group contained either 35, 60 or 80 mice and each test group contained either 13, 15 or 20 mice respectively. The mice were sensitised by subcutaneous injection into the flank with an emulsion (0.1 ml) consisting of a solution of methylated bovine serum albumin (m-BSA) (0.1 mg) in sterile aqueous sodium chloride solution (0.05 ml; 0.15M) and Complete Adjuvant (0.05 ml) containing, in total, Mycobacterium (0.075 mg). Simultaneously each mouse was injected intraperitoneally with an aqueous suspension of heat killed Bordetella Pertussis (0.05 ml; $2 \times 10^9$ organisms). Identical injections were administered after 7 days. After a further 14 days the left knee-joint of each mouse was injected with a solution of m-BSA (0.1 mg) in aqueous sodium chloride solution (0.01 ml; 0.15M) (intra-articular challenge). This procedure induced a chronic erosive arthritis restricted to the challenged joint.

The test compounds were suspended in a vehicle of aqueous carboxymethyl cellulose solution (0.25% w/v) containing TWEEN®80 (1.5% w/v) at varying dosages and 0.1 ml was administered to each test mouse by gastric intubation. The control mice received the vehicle with no test compound. Administration occurred daily for 28 days commencing 14 days after intra-articular challenge. After 42 days the test was terminated and the animals were killed using a rising concentration of carbon dioxide and the arthritic hind leg removed.

The femur and tibia were cut midway along their length and the knee-joint trimmed free of skin and musculature. The arthritic joints were placed in perforated plastic holders and fixed in 10% formol saline for at least 48 hours. They were then decalcified in 5% formic acid for 72 hours with constant agitation (replacing the formic acid after the first 24 hours), washed in water, dehydrated in alcohol and embedded in paraffin wax. The joints were sectioned in the sagittal plane at 5 μm and stained with Van Gieson's stain. Each joint was sectioned at two levels.

The severity of arthritis was assessed by examination of the prepared sections. Synovitis and pannus formation were graded on a 0–5 scale, by a skilled operator, according to the degree of synovial lining cell hypertrophy and hyperplasia, infiltration of the synovium by lymphocytes, plasma cells, monocytes/macrophages, fibroblasts and polymorphonuclear (PMN) leukocytes and the degree of pannus formation. Erosions of cartilage and bone were also graded on a 0–5 scale, by a skilled operator, the score reflecting the proportion of articular surface eroded as well as the depth of the erosions. Using the combined data the drug effects were expressed as the percentage change in the mean scores for synovitis and erosions compared to those of the control group. The data were then analysed using the Mann-Whitney U-test.

Those compounds which induced a statistically significant suppression of erosions or synovitis at a dosage of 100 mg/kg or below were deemed to be active. The results obtained are given in the Examples.

As an alternative to histological assessments, analysis of macerated specimens of tibial epiphyses using an image analysis system, may be used to assess the extent of hard tissue erosions. Active compounds are those which significantly reduce these erosions.

The invention is illustrated by the following non-limitative Examples in which parts and percentages are by weight and compositions of mixed solvents are given by volume. Novel compounds were characterised by elemental analysis and one or more of the following spectroscopic techniques: nuclear magnetic resonance, infra-red and mass spectroscopy.

In the Examples the following abbreviations are used: IMS=industrial methylated spirit, DMF=N,N-dimethylformamide and THF=tetrahydrofuran.

Unless otherwise stated, the starting materials used in the Examples were commercially available and may be obtained by reference to the Fine Chemicals Directory.

PREPARATION OF STARTING MATERIALS

EXAMPLE A1 a) 2-Chloro-5-nitropyridine (30.0 g) was added to a solution of sodium metal (4.4 g) in absolute ethanol (250 ml) under a nitrogen atmosphere. The mixture was boiled under reflux for 4 hours, then cooled slightly and filtered. The filtrate was cooled in ice and filtered to give 2-ethoxy-5-nitropyridine, m.p. 85°–88° C.

b) 2-Ethoxy-5-nitropyridine (12.0 g) in IMS (250 ml) was hydrogenated at ambient temperature at atmospheric pressure over 10% palladium charcoal (0.5 g). The catalyst was removed by filtration and the filtrate evaporated to give an oil. The oil was dissolved in ether, filtered and evaporated. A small sample of the oil was dissolved in ether and the solution saturated with hydrogen chloride gas. The mixture was filtered to give 5-amino-2-ethoxypyridine dihydrochloride, m.p. 203°–207° C. The remainder of the oil was used in part c) below.

c) 5-Amino-2-ethoxypyridine (9.25 g) and diethyl ethoxymethylenemalonate (14.5 g) was heated at 95° C. for 1 hour. On cooling in ice the oil solidified. The solid was ground up in petroleum ether (b.p. 60°–80° C.) and filtered to give diethyl 2-(6-ethoxy-3-pyridylaminomethylene) malonate, m.p. 68°–71° C.

d) The malonate from c) above (16.4 g) was added to diphenyl ether (100 ml) at 250° C. with stirring over 5 minutes. Heating was continued for a further 10 minutes and then the mixture was cooled to ambient temperature. Petroleum ether b.p. 60°–80° C. (100 ml) was added and the product was collected by filtration to give ethyl 6-ethoxy-4-hydroxy-1,5-naphthyridine-3-carboxylate, m.p. 275°–278° C.

EXAMPLE A2

Ethyl 4-hydroxy-6-methoxy-1,5-naphthyridine-3-carboxylate was prepared in a similar manner to that described in Example A1.

EXAMPLE A3 a) 2-Chloro-5-nitropyridine (4.48 g) was added in portions to a mixture of sodium phenoxide trihydrate (4.80 g) in DMF (140 ml) with stirring at ambient temperature under nitrogen. The mixture was then heated at 60° C. for 2 hours and then at 90° C. for 3 hours. The mixture was allowed to cool over 18 hours. The mixture was poured into ice water and extracted with dichloromethane to give a residue which was stirred in petroleum ether. b.p. 60°–80° C. at ambient temperature for 30 minutes and then filtered to give 5-nitro-2-phenoxypyridine, m.p. 84°–86° C.

b) The product from Part a) (14.9 g) was hydrogenated at ambient temperature in IMS (300 ml) using 10% palladium charcoal (0.5 g) as a catalyst. The catalyst was removed by filtration and the filtrate evaporated to give an oil which solidified on standing. A small sample (1.03 g) was dissolved in ether (50 ml) and the solution filtered to remove a small amount of insoluble material. The filtrate was saturated with hydrogen chloride gas and then filtered to give 5-amino-2-phenoxypyridine hydrochloride, m.p. 192°–195° C.

c) A mixture of 5-amino-2-phenoxypyridine (10.49 g) and diethyl ethoxymethylenemalonate (12.2 g) was boiled under reflux for 2.5 hours. The mixture was cooled to ambient temperature and water (50 ml) was added. The mixture was extracted with dichloromethane to give diethyl 2-(6-phenoxy-3-pyridylaminomethylene)malonate as an oil.

d) A solution of the malonate from Part c (18.8 g) in ethanol (25 ml) was added to diphenyl ether (100 ml) at 250°–260° C. over 30 minutes with stirring while allowing the ethanol formed to distil off. The mixture was boiled for 10 minutes after the addition and then cooled to ambient temperature. Petroleum ether. b.p. 60°–80° C. (100 ml) was added. The mixture was filtered to give ethyl 4-hydroxy-6-phenoxy-1,5-naphthyridine-3-carboxylate, m.p. 254°–7° C. (dec).

EXAMPLE A4 a) Diethyl methylmalonate (52.2 g) was added dropwise to a suspension of sodamide (11.7 g) in dry THF (150 ml) with stirring at ambient temperature under nitrogen. The mixture was boiled under reflux for 1 hour and then a solution of 2-chloro-5-nitropyridine (47.7 g) in dry THF (150 ml) was added dropwise cautiously with stirring. After the addition the mixture was boiled under reflux for 3 hours, then cooled and evaporated to remove approximately 80% of the solvent. The residue was poured into water (1 l) and extracted with ether to give an oil which partially crystallised on standing. A mixture of the residue, concentrated sulphuric acid (50 ml) and water (25 ml) was boiled under reflux for 4 hours then cooled in ice and neutralised using concentrated aqueous sodium hydroxide solution. The mixture was left to stand at ambient temperature for 64 hours and then filtered to give a solid which was extracted continuously with dichloromethane in a soxhlet extractor. The dichloromethane was cooled, dried and evaporated. The residue was filtered and the filtrate was distilled under vacuum to give 2-ethyl-5-nitropyridine, b.p. 82°–92° C. at 1 mm Hg.

b) 2-Ethyl-5-nitropyridine (16.3 g) was dissolved in IMS (200 ml) and hydrogenated at ambient temperature at 1 atmosphere using 10% palladium charcoal (0.5 g) as the catalyst. The mixture was filtered to remove the catalyst and the filtrate evaporated to give 5-amino-2-ethylpyridine as an oil.

c) A mixture of 5-amino-2-ethylpyridine (17.6 g) and diethyl ethoxymethylenemalonate (23.25 g) was heated on a steam bath for 2.5 hours. The mixture was cooled in ice. The solid formed was ground up in petroleum ether, b.p. 60°–80° C. and then filtered to give diethyl 2-(6-ethyl-3-pyridylaminomethylene)malonate, m.p. 55°–57° C.

d) The malonate (17.6 g) from c) was added in portions over 5 minutes to boiling diphenyl ether (100 ml) at 250°–260° C., with stirring, while allowing any ethanol formed to distil off. Heating was continued for 10 minutes after the addition and then the mixture was cooled. The mixture was diluted with petroleum ether. b.p. 60°–80° C. (125 ml) and filtered to give ethyl 6-ethyl-4-hydroxy-1,5-naphthyridine-3-carboxylate. m.p. 262°–264° C. (The compound contained approximately 20% of the isomeric 1,7-naphthyridine but was used without further purification).

EXAMPLE A5

Ethyl 3-ethoxy-8-hydroxypyrido[2,3-b]pyrazine-7-carboxylate was prepared as described in Chem. Pharm. Bull. 1974, 22 (8), 1864.

EXAMPLE A6 a) Sodium metal (46.2 g) was dissolved in absolute ethanol (1 l) with stirring under nitrogen. 3-Hydroxy-2-methylpyridine (200 g prepared as described in C.A. 48, P4597 h) was added. The mixture was stirred at ambient temperature for 30 minutes and then a solution of bromoethane (150 ml) in absolute ethanol (100 ml) was added. The mixture was boiled under reflux for 5 hours then cooled and filtered. The filtrate was evaporated and the residue partitioned between dichloromethane and water. The organic layer was separated off and the aqueous layer extracted with dichloromethane. The combined organic extracts were dried and evaporated. The residue was distilled to give 3-ethoxy-2-methyl-pyridine b.p. 80°–84° C. (20 mmHg).

b) 3-Ethoxy-2-methylpyridine (132.5 g) was added dropwise to concentrated sulphuric acid (530 ml) with stirring and cooling to keep the mixture below 10° C. A mixture of concentrated nitric acid (81 ml) and concentrated sulphuric acid (97 ml) was added dropwise over 4 hours, keeping the temperature below 5° C. The reaction mixture was allowed to warm up slowly to ambient temperature and then added in portions to ice/water (2.5 l). The solid was collected by filtration, washed with water and dried under vacuum at 50° C. to give 3-ethoxy-2-methyl-6-nitropyridine, m.p. 82°–84° C.

c) The nitropyridine above (176 g), IMS (1.6 l), reduced iron powder (179 g) and water (350 ml) were boiled under reflux. Heating was discontinued while concentrated hydrochloric acid (67 ml) was carefully added dropwise over 20 minutes. The mixture was boiled under reflux for 1.75 hours then cooled and filtered through a filtration aid. The filtrate was evaporated under reduced pressure. Water was added to the residue and the mixture basified with 5M sodium hydroxide. Extractive work-up (dichloromethane) gave 5-ethoxy-6-methylpyridin-2-amine, m.p. 93°–96° C.

d) A mixture of the amine from c) above (138 g) and diethyl ethoxymethylenemalonate (196 g) in IMS (190 ml) was boiled under reflux for 3 hours. The mixture was cooled and filtered to give diethyl 2-(5-ethoxy-6-methylpyrid-2-ylaminomethylene)malonate, m.p. 132°–138° C.

e) The malonate (118.3 g) from d) above was added to boiling diphenyl ether (1.5 l) over 10 minutes with stirring while allowing the ethanol formed to be removed by downward distillation. The mixture was boiled under reflux for 1.5 hours then cooled and diluted with petroleum ether b.p. 60°–80° C. (1.5 l). The solid was collected by filtration and washed with petroleum ether b.p. 60°–80° C. to give ethyl 6-ethoxy-4-hydroxy-7-methyl-1,8-naphthyridine-3-carboxylate, m.p. 255°–258° C.

f) A mixture of ethyl 6-ethoxy-4-hydroxy-7-methyl-1,8-naphthyridine-3-carboxylate (7.5 g), sodium hydroxide pellets (1.2 g) and water (20 ml) was heated at 180° C. with stirring in a sealed reaction vessel for 16 hours. The mixture was cooled to ambient temperature, filtered and the residue washed with water to give, after drying, 6-ethoxy-7-methyl-1,8-naphthyridin-4-ol, m.p. 278°–282° C. (with decomposition).

EXAMPLE A7 a) A mixture of 6-ethoxypyridin-2-amine (8.0 g) and diethyl ethoxymethylenemalonate (12.5 g) was heated at 95° C. under vacuum for 3 hours and then heated at 95° C. at atmospheric pressure for 18 hours. The mixture was cooled to ambient temperature, diluted with petroleum ether b.p. 40°–60° C. and filtered to give diethyl (6-ethoxy-2-pyridylamino)methylenemalonate, m.p. 58°–60° C.

b) The malonate from a) (15.3 g) was dissolved in diphenyl ether (50 ml) and added dropwise to boiling diphenyl ether (75 ml). The mixture was boiled under reflux for 45 minutes, then cooled and diluted with petroleum ether b.p. 60°–80° C. The mixture was filtered to give ethyl 7-ethoxy-4-hydroxy-1,8-naphthyridine-3-carboxylate, m.p. 175°–179° C.

EXAMPLE A8

Ethyl 4-hydroxy-7-methyl-6-propoxy-1,8-naphthyridine-3-carboxylate, m.p. 231°–235° C. was prepared from 3-hydroxy-2-methylpyridine in a similar manner to Example 6e.

EXAMPLE A9

Ethyl 4-hydroxy-7-methyl-1,8-naphthyridine-3-carboxylate was prepared as described in Aust. J. Chem., 1984, 1065.

EXAMPLE B1

Ethyl 6-ethoxy-4-hydroxy-1,5-naphthyridine-3-carboxylate (3.0 g) was added to phosphorus oxychloride (25 ml), with stirring, at ambient temperature. The mixture was heated at 50° C. for 45 minutes. The mixture was cooled to 10° C. and added to ice/water at less than 5° C. The mixture was then basified with concentrated aqueous ammonia solution SG 0.88 at less than 5° C. The mixture was extracted with dichloromethane to give ethyl 4-chloro-6-ethoxy-1,5-naphthyridine-3-carboxylate, m.p. 61°–64° C.

EXAMPLE B2

A mixture of ethyl 4-hydroxy-6-methoxy-1,5-naphthyridine-3-carboxylate (2.48 g) and phosphorus oxychloride (25 ml) was stirred and heated at 50°–55° C. for 30 minutes. The mixture was worked up as described in Example B1 to give ethyl 4-chloro-6-methoxy-1,5-naphthyridine-3-carboxylate, m.p. 98°–100° C.

EXAMPLE B3

A mixture of ethyl 4-hydroxy-6-phenoxy-1,5-naphthyridine-3-carboxylate (3.0 g) and phosphorus oxychloride (25 ml) was heated at 50° C. for 1 hour and then worked up as described in Example B1 to give ethyl 4-chloro-6-phenoxy-1,5-naphthyridine-3-carboxylate, m.p. 133°–137° C.

EXAMPLE B4

A mixture of ethyl 6-ethyl-4-hydroxy-1,5-naphthyridine-3-carboxylate (3.0 g) and phosphorus oxychloride (25 ml) was stirred and heated at 40°–50° C. for 1 hour. The mixture was then cooled and then worked up as described in Example B1 to give ethyl 4-chloro-6-ethyl-1,5-naphthyridine-3-carboxylate, m.p. 94°–96° C.

EXAMPLE B5

Ethyl 3-ethoxy-8-hydroxypyrido|2,3-b|pyrazine-7-carboxylate (2.5 g) was added to a stirred solution of phosphorus oxychloride (50 ml) with stirring. The mixture was heated at 50° C. for 3 hours and then worked up as described in Example B1 to give ethyl 8-chloro-3-ethoxypyrido|2,3-b|pyrazine-7-carboxylate which was used directly.

EXAMPLE B6

Ethyl 6-ethoxy-4-hydroxy-7-methyl-1,8-naphthyridine-3-carboxylate (2.5 g) was added to phosphorus oxychloride (20 ml) with stirring at ambient temperature. The mixture was warmed to 40° C. and kept at this temperature for 1 hour then cooled to 10° C. The mixture was added to excess ice/water and the mixture basified with aqueous ammonia solution (specific gravity 0.88) while keeping the temperature below 5° C. The product was extracted into dichloromethane. The combined dichloromethane extracts were evaporated under reduced pressure at ambient temperature to give ethyl 4-chloro-6-ethoxy-7-methyl-1,8-naphthyridine-3-carboxylate, m.p. >250° C.

EXAMPLE B7

In a similar manner to Example B1, 6-ethoxy-7-methyl-1,8-naphthyridin-4-ol (2.15 g) and phosphorus oxychloride (25 ml) were heated at 60° C. for 1 hour to give 5-chloro-3-ethoxy-2-methyl-1,8-naphthyridine, m.p. 164° C.

EXAMPLE B8

In a similar manner to Example B1, ethyl 7-ethoxy-4-hydroxy-1,8-naphthyridine-3-carboxylate (8.8 g) and phosphorus oxychloride (50 ml) were heated at 80° C. for 25 minutes to give ethyl 4-chloro-7-ethoxy-1,8-naphthyridine-3-carboxylate, m.p. 72°–75° C.

EXAMPLE B9 a) A mixture of ethyl 6-ethoxy-4-hydroxy-7-methyl-1,8-naphthyridine-3-carboxylate (5.0 g) and ethanol saturated with ammonia (80 ml) was stirred and heated in a sealed vessel at 210° C. (external temperature) for 20 hours. The mixture was cooled and filtered to give a solid. The filtrate was evaporated under reduced pressure and the residue was washed with ether, then water, to give a second crop of solid. $^1$H nmr showed that both crops contained 6-ethoxy-4-hydroxy-7-methyl-1,8-naphthyridine-3-carboxamide along with some starting material. The two crops were combined and used in b).

b) The combined solids from a) were added to phosphorus oxychloride (40 ml) at ambient temperature with stirring. The mixture was then heated on a steam bath with stirring for 1.5 hours and then cooled to 10° C. The mixture was then worked up as described in Example B1 to give 4-chloro-6-ethoxy-7-methyl-1,8-naphthyridine-3-carbonitrile which contained some ester but was used without further purification.

EXAMPLE B10

Ethyl 4-chloro-7-methyl-6-propoxy-1,8-naphthyridine-3-carboxylate, m.p. 100°–106° C. was prepared in a similar manner to Example B6, starting from the product of Example A8.

EXAMPLE B11

5-Chloro-2-methyl-1,8-naphthyridine was prepared as described in Aust. J. Chem., 1984, 37, 1065.

EXAMPLE B12 a) A mixture of ethyl 6-ethoxy-4-hydroxy-7-methyl-1,8-naphthyridine-3-carboxylate (10.0 g), 5M sodium hydroxide solution (200 ml), IMS (64 ml) and water (64 ml) was boiled under reflux for 2 hours. The mixture was cooled to ambient temperature and then filtered. The residue was dissolved in water, acidified to pH5 with glacial acetic acid and filtered. The residue was triturated with hot IMS, cooled and filtered to give 6-ethoxy-4-hydroxy-7-methyl-1,8-naphthyridine-3-carboxylic acid, m.p. 259°–261° C.

b) 6-Ethoxy-4-hydroxy-7-methyl-1,8-naphthyridine-3-carboxylic acid (8.7 g) was added with stirring to phosphorus oxychloride (75 ml) at ambient temperature. The mixture was heated at 60° C. (internal temperature) for 45 minutes and then cooled to 10° C. The mixture was added dropwise to aqueous ammonia solution (specific gravity 0.88) at 10° C. over 4 hours. The mixture was filtered and the solid obtained was washed with absolute ethanol (7×100 ml). The combined washings were evaporated under reduced pressure to give 4-chloro-6-ethoxy-7-methyl-1,8-naphthyridine-3-carboxamide, which was used without further purification.

EXAMPLE B13

Ethyl 4-chloro-7-methyl-1,8-naphthyridine-3-carboxylate, m.p. 89°–90° C., was prepared from the product of Example A9 in an analogous manner to Example B6.

EXAMPLE C1 a) 4-Nitrophenoxyacetic acid (10.2 g) was added to thionyl chloride (50 ml) and the mixture was boiled under reflux for 1.5 hours. Excess thionyl chloride was distilled off and the residue was heated with toluene (2×50 ml) and the toluene removed by distillation to leave an oil which solidified on cooling. The acid chloride was added in portions to a stirred mixture of absolute ethanol (50 ml) and concentrated aqueous ammonia (50 ml, SG 0.880) at 10°–15° C. The mixture was stirred for 45 minutes at 10°–15° C. and then allowed to warm up to ambient temperature. The mixture was filtered to give 4-nitrophenoxyacetamide, m.p. 153°–155° C.

b) The product from a) (8.3 g) was suspended in IMS (250 ml) and hydrogenated at ambient temperature at 1 atmosphere using 10% palladium charcoal (0.5 g) as catalyst. The catalyst was removed by filtration and the filtrate was evaporated to dryness. The residue was triturated with petroleum ether, b.p. 60°–80° C. and filtered to give 4-aminophenoxyacetamide, m.p. 123°–125° C.

EXAMPLE C2

A mixture of 5-aminosalicylic acid (15 g), absolute ethanol (250 ml) and concentrated sulphuric acid (7.5 ml) was boiled under reflux with stirring for 8.5 hours. The reaction mixture was evaporated to dryness. Water (20 ml) was added to the residue and the mixture filtered. The filtrate was basified with saturated bicarbonate solution and the solid collected by filtration. The solid was extracted into dichloromethane and the extract evaporated to dryness. The residue was triturated with petroleum ether b.p. 40°–60° C. and filtered to give ethyl 5-aminosalicylate, m.p. 44° C.

EXAMPLE C3

4-Aminophenol (27.3 g) in DMF (200 ml) was added dropwise over 30 minutes to a stirred suspension of sodium hydride (10.0 g, 60% dispersion in mineral oil) in DMF (200 ml) with stirring under nitrogen. When the evolution of hydrogen had ceased, 2-bromopyridine (39.5 g) was added and the resultant solution was heated at 120° C. for 6 hours. The DMF was removed under reduced pressure, the residue was dissolved in water (250 ml) and the mixture extracted with dichloromethane. The combined organic extracts were washed with water, 1M sodium hydroxide solution and then again with water and then with 2M hydrochloric acid. The acid extracts were basified and extracted with dichloromethane to give an oil which solidified on standing. This solid was triturated in petroleum ether, b.p. 40°–60° C./ethyl acetate (10:1) to give 4-(2-pyridyloxy)aniline, m.p. 64°–67° C.

EXAMPLE C4 a) Sodium hydride (1.53 g, 60% dispersion in mineral oil) was added in portions to a solution of 1,2:5,6-di-O-isopropylidene-D-glucofuranose (10.0 g) in DMF (40 ml) and toluene (80 ml) with stirring under nitrogen. The mixture was boiled under reflux for 15 minutes then cooled and 4-fluoronitrobenzene (5.4 g) was added. The resulting solution was boiled under reflux for 5 hours. The mixture was cooled and washed with water. The organic phase was separated, dried and evaporated under reduced pressure. The residue was recrystallised from IMS to give 1,2:5,6-di-O-isopropylidene-3-O-(4-nitrophenyl)-D-glucofuranose, m.p. 122°–126° C.

b) The product from Part 1 (5.0 g) was hydrogenated in absolute ethanol (300 ml) in the presence of 10% palladium on charcoal (150 mg) at atmospheric pressure. The reaction mixture was filtered to remove the catalyst and the filtrate was concentrated under reduced pressure to give 3-O-(4-aminophenyl)-1,2:5,6-di-O-isopropylidene-D-glucofuranose which was used without further purification.

PREPARATION OF EXAMPLES OF THE INVENTION

Example 1

A mixture of ethyl 4-chloro-6-ethoxy-1,5-naphthyridine-3-carboxylate (3.1 g), 4-methoxyaniline (1.36 g) and IMS (40 ml) was boiled under reflux for 4 hours. The mixture was evaporated to dryness. The residual solid was ground in ether and then filtered. The solid was dissolved in dichloromethane and purified by column chromatography on silica using dichloromethane, then ether, then ethyl acetate, then IMS, as the mobile phase. The third fraction obtained was dissolved in IMS (30 ml) and the solution was saturated with hydrogen chloride gas. Ether was added and the mixture left to stand at approximately 4° C. for 3 days. The mixture was filtered to give ethyl 6-ethoxy-4-(4-methoxyanilino)-1,5-naphthyridine-3-carboxylate hydrochloride hydrate, m.p. 130°–133° C. Active (3/3) at 30 mg/kg.

Example 2

A mixture of ethyl 4-chloro-6-ethoxy-1,5-naphthyridine-3-carboxylate (17.95 g), 4-methoxyaniline (8.29 g), anhydrous potassium carbonate (18.6 g) and THF (250 ml) was stirred at ambient temperature for 48 hours. The mixture was evaporated to dryness and water was added to the residue. The mixture was extracted with dichloromethane to give a solid which was dissolved in IMS (50 ml). The solution was saturated with hydrogen chloride gas whilst cooling the mixture in ice. Ether was added to induce precipitation. The solid was collected by filtration to give ethyl 6-ethoxy-4-

(4-methoxyanilino)-1,5-naphthyridine-3-carboxylate hydrochloride, m.p. 160°–162° C. Active (3/3) at 30 mg/kg.

Example 3

A mixture of ethyl 4-chloro-6-ethoxy-1,5-naphthyridine-3-carboxylate (2.41 g), 4-(2-diethylamino)ethoxyaniline (2.04 g), anhydrous potassium carbonate (2.49 g) and THF (70 ml) was stirred at ambient temperature for 72 hours. The mixture was filtered and the filtrate evaporated to give an oil which solidified on standing. The solid was ground in ether and filtered. The filtrate was evaporated and the residue purified by chromatography on silica using ethyl acetate as a mobile phase to remove impurities followed by dichloromethane:IMS (9:1) as a mobile phase to elute the product. The product was obtained as an oil which was dissolved in IMS (25 ml). The solution was saturated with hydrogen chloride gas with cooling. Ether was added to induce crystallisation. The solid was collected by filtration to give ethyl 6-ethoxy-4-|4-(2-diethylaminoethoxy)anilino|-1,5-naphthyridine-3-carboxylate dihydrochloride, m.p. 188°–189° C.

Example 4

A mixture of ethyl 4-chloro-6-methoxy-1,5-naphthyridine-3-carboxylate (1.68 g), 4-methoxyaniline (0.78 g), dry THF (50 ml) and anhydrous potassium carbonate (1.74 g) was stirred at ambient temperature for 7 hours. Further amounts of 4-methoxyaniline (0.4 g) and anhydrous potassium carbonate (0.9 g) were added and the mixture stirred at ambient temperature for 32 hours. The mixture was evaporated to dryness and the residue diluted with water (100 ml). The mixture was extracted into dichloromethane to give an oil which solidified. The solid was purified by column chromatography on silica using ethyl acetate as the mobile phase to give ethyl 6-methoxy-4-(4-methoxyanilino)-1,5-naphthyridine-3-carboxylate, m.p. 115°–117° C.

Example 5

A mixture of ethyl 4-chloro-6-ethoxy-1,5-naphthyridine-3-carboxylate (3.30 g) 4-(2-pyridyloxy)aniline (2.25 g), anhydrous potassium carbonate (3.43 g) and THF (90 ml) was stirred at ambient temperature for 72 hours. The mixture was filtered and the filtrate evaporated to dryness to give a residue which was dissolved in IMS (50 ml). This solution was saturated with hydrogen chloride gas with cooling in ice. The mixture was filtered and the solid collected was discarded. The filtrate was cooled in ice and diluted with ether. The mixture was filtered and the solid which was collected was dissolved in warm IMS and reprecipitated with ether. The mixture was again filtered and the filtrate was evaporated to dryness. The residue was purified by flash chromatography on silica using dichloromethane:IMS (19:1) as the mobile phase. The solid obtained was recrystallised from IMS to give ethyl 6-ethoxy-4-|4-(2-pyridyloxy)anilino|-1,5-naphthyridine-3-carboxylate, m.p. 148°–151° C. Active (1/1) at 30 mg/kg.

Example 6

A mixture of ethyl 4-chloro-6-ethoxy-1,5-naphthyridine-3-carboxylate (2.1 g), 2-ethoxy-5-aminopyridine (1.08 g), anhydrous potassium carbonate (2.17 g) and THF (60 ml) was stirred at ambient temperature for 48 hours. The mixture was evaporated to dryness and water added to the residue. The mixture was extracted with dichloromethane to give an oily solid. This solid was dissolved in IMS (20 ml) and the solution saturated with hydrogen chloride gas while cooling in ice. Ether was added to induce precipitation. The mixture was filtered to give ethyl 6-ethoxy-4-(2-ethoxy-5-pyridylamino)-1,5-naphthyridine-3-carboxylate hydrochloride, m.p. 187°–189° C. Borderline active (1/1) at 30 mg/kg.

Example 7

A mixture of ethyl 4-chloro-6-ethoxy-1,5-naphthyridine-3-carboxylate (2.4 g), 4-(2-hydroxyethoxy)aniline (1.4 g), anhydrous potassium carbonate (2.49 g) and THF (70 ml) was stirred at ambient temperature for 3 days. The mixture was filtered and the filtrate evaporated to dryness. The residue was ground up in ether and filtered. The residue was dissolved in dichloromethane and purified by chromatography on silica. The product fractions were combined, dissolved in IMS (150 ml) and saturated with hydrogen chloride gas. The mixture was cooled in ice and diluted with ether to induce precipitation. The mixture was filtered to give ethyl 6-ethoxy-4-|4-(2-hydroxyethoxy)anilino|-1,5-naphthyridine-3-carboxylate hydrochloride, m.p. 177°–178° C.

Example 8

A mixture of ethyl 4-chloro-6-ethoxy-1,5-naphthyridine-3-carboxylate (0.86 g), 4-aminophenyl-β-D-galactopyranoside (0.84 g) and IMS (30 ml) was boiled under reflux for 1 hour. The mixture was cooled in ice and then filtered to give ethyl 6-ethoxy-4-|4-(β-D-galactopyranosyl)anilino|-1,5-naphthyridine-3-carboxylate hemihydrochloride, m.p. 189°–191° C.

Example 9

A mixture of ethyl 4-chloro-6-phenoxy-1,5-naphthyridine-3-carboxylate (3.0 g), 4-methoxyaniline (1.16 g), potassium carbonate (2.65 g) and THF (60 ml) was stirred at ambient temperature for 24 hours. The reaction mixture was worked up as described in Example 2 to give ethyl 4-(4-methoxyanilino)-6-phenoxy-1,5-naphthyridine-3-carboxylate hydrochloride, m.p. 191°–193° C.

Example 10

A mixture of 4,7-dichloro-1,5-naphthyridine (0.65 g), 4-methoxyaniline (0.40 g) and IMS (25 ml) was boiled under reflux for 5 hours. The mixture was concentrated to approximately 5 ml and then ether added to induce precipitation. Ethyl acetate was added and the solid was collected by filtration to give 7-chloro-4-(4-methoxyanilino)-1,5-naphthyridine hydrochloride hydrate m.p. 230°–233° C.

Example 11

A mixture of ethyl 4-chloro-6-ethyl-1,5-naphthyridine-3-carboxylate (2.1 g), 4-methoxyaniline (1.0 g) and IMS (50 ml) was boiled under reflux for 2.5 hours. The mixture was evaporated under reduced pressure to give an oil which was purified by flash column chromatography on silica using dichloromethane/IMS, 19:1 as the mobile phase to give the product as an oil which was dissolved in methanol (15 ml). This solution was saturated with hydrogen chloride gas and then diluted with ether, with cooling. The solid was collected by filtration to give ethyl 6-ethyl-4-(4-methoxyanilino)-1,5-naphthyridine-3-carboxylate, m.p. 145°–148° C.

Example 12

A mixture of ethyl 4-chloro-6-ethoxy-1,5-naphthyridine-3-carboxylate (2.0 g), absolute ethanol (30 ml) and 4-(2,3- dihydroxypropoxy)aniline (1.38 g) was boiled under reflux for 1 hour. The reaction mixture was hot filtered and the filtrate evaporated to dryness. The residue was triturated with dichloromethane and filtered. The filtrate was evaporated to dryness and the residue was purified by column chromatography on silica using ethyl acetate as the mobile phase to give ethyl 6-ethoxy-4-|4-(2,3-dihydroxypropoxy) anilino|-1,5-naphthyridine-3-carboxylate, m.p. 143°–145° C.

Example 13

A mixture of ethyl 8-chloro-3-ethoxypyrido|2,3-b|-pyrazine-7-carboxylate (2.32 g) and 4-methoxyaniline (1.0 g) in ethanol (40 ml) was boiled under reflux for 1 hour. The mixture was allowed to cool and the solvent removed under reduced pressure. The residue was triturated with hot ethyl acetate and filtered to give a solid which was recrystallised from ethyl acetate to give a solid which was purified by chromatography on silica to give ethyl 3-ethoxy-8-(4-methoxyanilino)pyrido|2,3-b|pyrazine-7-carboxylate sesquihydrochloride hydrate, m.p. 143°–145° C.

Example 14

A mixture of ethyl 4-chloro-6-ethoxy-1,5-naphthyridine-3-carboxylate (2.0 g), ethyl 5-aminosalicylate (1.37 g) and absolute alcohol (30 ml) was boiled under reflux for 3 hours and then cooled to ambient temperature. The mixture was filtered to give a solid which was recrystallised from IMS to give ethyl 5-(6-ethoxy-3-ethoxycarbonyl-1,5-naphthyridin-4-ylamino) salicylate hydrochloride, m.p. 204°–206° C.

Example 15 a) The mixture of 5-chloro-3-ethoxy-2-methyl-1,8-naphthyridine (5.0 g), 4-methoxyaniline (2.77 g) and IMS (40 ml) was boiled under reflux for 2.5 hours. The mixture was cooled and filtered. The solid obtained was dissolved in boiling IMS (50 ml) and 5M sodium hydroxide solution (4.0 ml) was added. The mixture was heated under reflux for 1 hour and then cooled and water (100 ml) was added. The mixture was filtered to give 3-ethoxy-5-(4-methoxyanilino)-2-methyl-1,8-naphthyridine hydrate, m.p. 228°–231° C.

b) The product from a) (2.0 g) was suspended in dichloromethane (30 ml) and added to a suspension of anhydrous aluminium chloride (4.3 g) in dichloromethane (37.5 ml) with stirring at ambient temperature. The mixture was stirred for 24 hours, then more aluminium chloride (4.3 g) was added and the mixture stirred for a further 24 hours, then poured into ice water and stirred for 10 minutes. The solid was collected by filtration, washed well with ether, dried and then recrystallised from IMS to give 3-hydroxy-5-(4-methoxyanilino)-2-methyl-1,8-naphthyridine, m.p. 169°–174° C.

c) Acetoxyacetyl chloride (1.0 ml) was added dropwise to a stirred mixture of the product from b) (2.2 g), N,N-dimethylaniline (1.0 g) and dichloromethane (75 ml) at ambient temperature. The mixture was boiled under reflux for 2 hours and then cooled and filtered. The product was dissolved in IMS then cooled and precipitated with ether. The product was collected by filtration, dissolved in IMS, hot filtered and then precipitated with ether to give 5-(4-methoxyanilino)-2-methyl-1,8-naphthyridin-3-yl acetoxyacetate, m.p. 213°–216° C. Active (1/1) at 30 mg/kg.

Example 16 a) A mixture of ethyl 4-chloro-6-ethoxy-7-methyl-1,8-naphthyridine-3-carboxylate (3.5 g) and 4-methoxyaniline (1.5 g) in ethanol (50 ml) was boiled under reflux for 1.5 hours. The mixture was concentrated to half the volume, cooled and ether added. The solid was collected by filtration to give ethyl 6-ethoxy-4-(4-methoxyanilino)-7-methyl-1,8-naphthyridine-3-carboxylate hydrochloride, m.p. 260°–262° C.

b) A mixture of the product from a) (4.76 g), glyoxylic acid (1.73 g) and glacial acetic acid (50 ml) was boiled under reflux for 24 hours. The mixture was cooled and the solid was collected by filtration. The filtrate was acidified with concentrated hydrochloric acid and filtered to give a second crop of solid. The two crops of solid were combined, stirred in water and the mixture basified with sodium bicarbonate. The pH of the mixture was adjusted to pH 6 with concentrated hydrochloric acid and the mixture was extracted with ethyl acetate and then with dichloromethane. The combined organic extracts were washed with water, dried and evaporated. The residue was triturated with ethyl acetate and then filtered to give 3-|3-ethoxy-6-ethoxycarbonyl-5-(4-methoxyanilino)-1,8-naphthyridin-2-yl|acrylic acid hemihydrochloride, m.p. 259°–261° C.

c) A mixture of the product from b) (4.0 g), triethylamine (1.45 g) and DMF (300 ml) was stirred in an ice bath and treated with ethyl chloroformate (a molar equivalent). The solution was stirred at 0° C. for 1 hour and then concentrated aqueous ammonia solution (3 ml, SG 0.88) was added. The mixture was shaken with dichloromethane and aqueous sodium bicarbonate solution. The organic extract was separated, washed with sodium bicarbonate solution, water, dried and evaporated to give a liquid and a solid. This mixture was triturated with ether to give a solid which was purified by chromatography on silica using dichloromethane with gradually increasing amounts of methanol to give a solid which was recrystallised from ethanol/dichloromethane to give ethyl 7-(2-carbamoylvinyl)-6-ethoxy-4-(4-methoxyanilino)-1,8-naphthyridine-3-carboxylate, m.p. 238°–242° C.

Example 17

A mixture of ethyl 4-chloro-6-ethoxy-7-methyl-1,8-naphthyridine-3-carboxylate (2.4 g), 5-amino-2-ethoxypyridine (1.15 g) and IMS (50 ml) was boiled under reflux for 1.5 hours. The mixture was cooled and filtered to give ethyl 6-ethoxy-4-(2-ethoxy-5-pyridylamino)-7-methyl-1,8-naphthyridine-3-carboxylate hydrochloride, m.p. 221°–223° C. Active (1/1) at 30 mg/kg.

Example 18

A mixture of 5-chloro-3-ethoxy-2-methyl-1,8-naphthyridine (2.0 g), 5-aminopyridin-2-ol (1.0 g) and IMS (20 ml) was boiled under reflux for 2 hours. The mixture was cooled and filtered to give 5-(3-ethoxy-2-methyl-1,8-naphthyridin-5-ylamino)pyridin-2-ol hydrochloride sesquihydrate, m.p. 295°–300° C.

Example 19

A mixture of 5-chloro-3-ethoxy-2-methyl-1,8-naphthyridine (2.0 g), 5-amino-2-ethoxypyridine (1.25 g) and IMS (20 ml) was boiled under reflux for 2 hours. The mixture was cooled and filtered to give 3-ethoxy-5-(2-ethoxy-5-pyridylamino)-2-methyl-1,8-naphthyridine hydrochloride dihydrate, m.p. 184°–187° C. Active (2/3) at 30 mg/kg.

Example 20

A mixture of ethyl 4-chloro-7-ethoxy-1,8-naphthyridine-3-carboxylate (1.6 g) and 5-amino-2-ethoxypyridine (0.8 g)

and IMS (50 ml) was boiled under reflux for 2 hours. The mixture was cooled and ether (200 ml) was added. The mixture was filtered to give ethyl 7-ethoxy-4-(2-ethoxy-5-pyridylamino)-1,8-naphthyridine-3-carboxylate hydrochloride, m.p. 180°–185° C. Active (1/1) at 30 mg/kg.

Example 21

A mixture of 5-chloro-3-ethoxy-2-methyl-1,8 naphthyridine (0.98 g), 6-amino-2-ethoxypyridine (0.6 g), IMS (25 ml) and concentrated hydrochloric acid (2 drops) was boiled under reflux for 18 hours. The mixture was cooled and filtered to give 3-ethoxy-5-(6-ethoxy-2-pyridylamino)-2-methyl-1,8-naphthyridine hydrochloride, m.p. >250° C. Active (1/1) at 30 mg/kg.

Example 22

A mixture of ethyl 4-chloro-6-ethoxy-7-methyl-1,8-naphthyridine-3-carboxylate (1.3 g), 6-amino-2-ethoxy pyridine (0.68 g), IMS (25 ml) and concentrated hydrochloric acid (2 drops) was boiled under reflux for 18 hours. The mixture was cooled and filtered to give ethyl 6-ethoxy-4-(6-ethoxy-2-pyridylamino)-7-methyl-1,8-naphthyridine-3-carboxylate sesquihydrochloride hydrate, m.p. 195°–200° C. Active (1/1) at 30 mg/kg.

Example 23

A mixture of 4-chloro-6-ethoxy-7-methyl-1,8-naphthyridine-3-carbonitrile (2.66 g), 4-methoxyaniline (1.35 g) and IMS (50 ml) was boiled under reflux for 2.5 hours. The mixture was cooled in ice and the precipitate was collected by filtration. This solid was boiled in IMS (50 ml), with 5M sodium hydroxide solution (1.2 ml) under reflux for 30 minutes. The mixture was cooled and evaporated. The residue was purified by flash chromatography on silica using dichloromethane/IMS, 19:1 as the mobile phase to give a solid which was ground up in IMS (15 ml) and filtered to give 6-ethoxy-4-(4-methoxyanilino)-7-methyl-1,8-naphthyridine-3-carbonitrile, m.p. 190°–192° C. Active (1/1) at 30 mg/kg.

Example 24

A mixture of ethyl 4-chloro-6-ethoxy-7-methyl-1,8-naphthyridine-3-carboxylate (2.0 g), 4-aminophenoxy acetamide (1.13 g) and absolute ethanol (30 ml) was boiled under reflux for 1 hour and then cooled to ambient temperature. The mixture was filtered to give ethyl 4-[4-(carbamoylmethoxy)anilino]-6-ethoxy-7-methyl-1,8-naphthyridine-3-carboxylate hydrochloride, m.p. 215°–217° C.

Example 25

A mixture of ethyl 4-chloro-6-ethoxy-7-methyl-1,8-naphthyridine-3-carboxylate (2.0 g), 5-aminopyrimidine-2,4-diol (0.86 g) and IMS (25 ml) was boiled under reflux for 3 hours. The mixture was concentrated to approximately 15 ml, then cooled at 0° C. The mixture was filtered to give ethyl 4-(2,4-dihydroxy-5-pyrimidinylamino)-6-ethoxy-7-methyl-1,8-naphthyridine-3-carboxylate hemihydrochloride dihydrate, m.p. 250° C. Active (1/1) at 30 mg/kg.

Example 26

A mixture of 5-chloro-2-methyl-1,8-naphthyridine (1.8 g), 5-amino-2-(pyrid-3-yloxy)pyridine (1.87 g) and IMS (35 ml) was boiled under reflux for 5 hours. The mixture was cooled to ambient temperature and filtered to give a solid which was recrystallised from IMS to give 2-methyl-5-[2-(pyrid-3-yloxy)pyrid-5-ylamino]-1,8-naphthyridine hydrochloride 2.5 hydrate, m.p. 235°–237° C. Borderline active (1/1) at 30 mg/kg.

Example 27

A mixture of ethyl 4-chloro-6-ethoxy-7-methyl-1,8-naphthyridine-3-carboxylate (2.3 g), 5-amino-2-phenoxypyridine (1.52 g) and IMS (50 ml) was boiled under reflux for 2 hours. The mixture was cooled in ice and filtered to give ethyl 6-ethoxy-7-methyl-4-(2-phenoxy-5-pyridylamino)-1,8-naphthyridine-3-carboxylate hydrochloride, m.p. 220°–221° C.

Example 28

A mixture of ethyl 4-chloro-6-ethoxy-7-methyl-1,8-naphthyridine-3-carboxylate (3.1 g), 4-aminophenoxyacetic acid hydrochloride (2.17 g) (prepared by reduction of 4-nitrophenoxyacetic acid using hydrogen and 10% palladium charcoal in a similar manner to Example C1 followed by treatment with 5M hydrochloric acid and then evaporation) and absolute ethanol (30 ml) was boiled under reflux for 4 hours. The mixture was cooled to ambient temperature and filtered to give ethyl 4-(6-ethoxy-3-ethoxycarbonyl-7-methyl-1,8-naphthyridin-4-ylamino) phenoxyacetate hydrochloride, m.p. 192°–194° C. Active (1/1) at 30 mg/kg.

Example 29

A mixture of ethyl 4-chloro-6-ethoxy-7-methyl-1,8-naphthyridine-3-carboxylate (2.0 g), absolute ethanol (30 ml) and ethyl 5-aminosalicylate (1.23 g) was boiled under reflux for 1 hour. The mixture was cooled to ambient temperature and filtered to give a solid which was recrystallised from IMS to give ethyl 5-(6-ethoxy-3-ethoxycarbonyl-7-methyl-1,8-naphthyridin-4-ylamino) salicylate hydrochloride, m.p. 208°–210° C.

Example 30

A solution of 3-O-(4-aminophenyl)-1,2:5,6-di-O-isopropylidene-D-glucofuranose (2.22 g) in a minimal volume of IMS was added to a solution of ethyl 4-chloro-6-ethoxy-7-methyl-1,8-naphthyridine-3-carboxylate (1.87 g) in IMS (40 ml). The mixture was boiled under reflux for 18 hours. The mixture was evaporated to dryness under reduced pressure and the solid residue was recrystallised from ethanol/ether to give 3-O-[4-(6-ethoxy-3-ethoxycarbonyl-7-methyl-1,8-naphthyridin-4-ylamino)phenyl]-1,2-O-isopropylideneglucofuranose hydrochloride, m.p. 153°–159° C.

Example 31

A solution of p-aminophenyl galactopyranoside (1.83 g) in a minimal volume of ethanol was added to a solution of ethyl 4-chloro-6-ethoxy-7-methyl-1,8-naphthyridine-3-carboxylate (2.0 g) in absolute ethanol (40 ml). The mixture was boiled under reflux for 18 hours and then cooled and triturated with ether giving an oil. The supernatant solution was decanted away from the oil and this solution was triturated with more ether to produce a solid which was collected by filtration to give ethyl 6-ethoxy-4-[4-(β-D-galactopyranosyl)anilino]-7-methyl-1,8-naphthyridine-3-carboxylate hydrochloride, m.p. 150°–153° C. Active (1/2) at 30 mg/kg.

Example 32

A solution of 4-aminophenyl-β-D-galactopyranoside (2.08 g) in IMS (50 ml) was added to a solution of 5-chloro-3-ethoxy-2-methyl-1,8-naphthyridine (1.7 g) in IMS (30 ml). The mixture was boiled under reflux for 18 hours. The mixture was cooled and filtered to give 4-(6-ethoxy-7-methyl-1,8-naphthyridin-4-ylamino)phenyl β-D-galactopyranoside hydrochloride. m.p. 223°–225° C. Active (1/1) at 30 mg/kg.

Example 33

A solution of 3-O-(4-aminophenyl-1,2:5,6-di-O-isopropylidene-D-glucofuranose (3.15 g) in a minimal amount of IMS was added to a solution of 5-chloro-3-ethoxy-2-methyl-1,8-naphthyridine (2.0 g) in IMS (40 ml). The mixture was boiled under reflux for 18 hours and then concentrated under reduced pressure to approximately 75% of its original volume. This solution was triturated with ether to induce precipitation. The solid was collected by filtration and recrystallised from IMS/ether to give 3-O-|4-(6-ethoxy-7-methyl-1,8-naphthyridin-4-ylamino)phenyl|-1,2:5,6-di-O-isopropylidene-D-glucofuranose hydrochloride. m.p. 251°–254° C.

Example 34

A suspension of 4-aminophenyl-β-D-lactopyranoside (1.0 g) in IMS (40 ml) was added to a solution of ethyl 4-chloro-6-ethoxy-7-methyl-1,8-naphthyridine-3-carboxylate (0.68 g) in IMS (20 ml). The mixture was boiled under reflux for 18 hours, then cooled and triturated with ether. The solid was collected by filtration to give ethyl 6-ethoxy-4-|4-(β-D-lactopyranosyl)anilino|-7-methyl-1,8-naphthyridine-3-carboxylate hydrochloride dihydrate. m.p. 180°–183° C. Active (1/1) at 30 mg/kg.

Example 35

A solution of 4-aminophenyl-β-D-lactopyranoside (1.0 g) in a minimal volume of IMS was added to a solution of 4-chloro-6-ethoxy-7-methyl-1,8-naphthyridine-3-carboxamide (prepared from the product of Example B9a in an analogous manner to Example B6) (0.61 g) in IMS (40 ml). The mixture was boiled under reflux for 3.5 hours, then cooled and triturated with ether. The solid was collected by filtration to give 6-ethoxy-4-|4-(β-D-lactopyranosyl)anilino|-7-methyl-1,8-naphthyridine-3-carboxamide hydrochloride sesquihydrate. m.p. 176°–180° C.

Example 36

A mixture of ethyl 4-chloro-7-methyl-6-propoxy-1,8-naphthyridine-3-carboxylate (1.3 g), 4-aminophenyl-β-D-galactopyranoside (1.17 g) and IMS (40 ml) was boiled under reflux for 4 hours. The mixture was cooled at ambient temperature overnight and then cooled in ice and ether added to induce precipitation. The solid was collected by filtration and dissolved in hot IMS (75 ml), cooled in ice and precipitated with ether. The solid was collected by filtration and the crystallisation process repeated. The solid obtained was purified by chromatography on silica using dichloromethane/IMS, 4:1 as the mobile phase to give ethyl 4-|4-(β-D-galactopyranosyl)anilino|-7-methyl-6-propoxy-1,8-naphthyridine-3-carboxylate hydrochloride sesquihydrate. m.p. 148°–52° C. (dec).

Example 37

A mixture of 2-methyl-5-chloro-1,8-naphthyridine (2.0 g), 4-(2-pyridyloxy)aniline (2.1 g) and IMS (50 ml) was boiled under reflux for 3.5 hours. The mixture was cooled and filtered to give a solid. The solid was suspended in IMS (770 ml) and hydrogen chloride gas was bubbled through the mixture while the mixture was cooled in an ice bath. The mixture was then warmed until all the solid had dissolved and then cooled in an ice bath and further hydrogen chloride gas was bubbled through. After standing at 0° C. for 3 minutes, ethyl acetate (approximately 150 ml) was added and the precipitate was collected by filtration to give 2-methyl-5-|4-(2-pyridyloxy)anilino|-1,8-naphthyridine hydrochloride hydrate. m.p. 299°–305° C. Active (1/2) at 30 mg/kg.

Example 38

A mixture of ethyl 4-chloro-7-methyl-1,8-naphthyridine-3-carboxylate (2.49 g) and 4-(2-pyridyloxy)aniline (1.85 g) in IMS (50 ml) was boiled under reflux for 1 hour. The mixture was allowed to stand at ambient temperature overnight and then evaporated under reduced pressure. The residue was triturated with ethyl acetate and filtered to give a solid which was recrystallised from ethanol/ethyl acetate. This solid was dissolved in IMS and hydrogen chloride gas was bubbled through the solution with cooling. The solvent was then evaporated under reduced pressure and the residue was recrystallised from ethanol/ethyl acetate to give ethyl 7-methyl-4-|4-(2-pyridyloxy)anilino|-1,8-naphthyridine-3-carboxylate hydrochloride. m.p. 207°–208° C. Active (2/2) at 30 mg/kg.

Example 39

A mixture of 4-chloro-6-ethoxy-7-methyl-1,8-naphthyridine-3-carboxylate (1.6 g) and 4-(2-pyridyloxy)aniline (1.0 g) and IMS (50 ml) was boiled under reflux for 1 hour and then allowed to stand at ambient temperature overnight. The mixture was evaporated under reduced pressure and the residue was recrystallised from ethyl acetate/IMS to give a solid which was dissolved in IMS with warming to give a solution. The solution was cooled in an ice bath and hydrogen chloride gas was bubbled through the mixture. The solid was collected by filtration to give ethyl 6-ethoxy-7-methyl-4-|4-(2-pyridyloxy)anilino|-1,8-naphthyridine-3-carboxylate dihydrochloride. m.p. 223°–224° C. Active (1/1) at 30 mg/kg.

Example 40

A mixture of 5-chloro-3-ethoxy-2-methyl-1,8-naphthyridine (2.0 g) and 4-(2-pyridyloxy)aniline (1.67 g) in IMS (50 ml) was boiled under reflux for 3 hours and then allowed to stand at ambient temperature overnight. The mixture was evaporated under reduced pressure and the residue recrystallised from IMS to give a solid which was dissolved in hot IMS and then cooled in an ice bath while hydrogen chloride gas was bubbled through. The mixture was evaporated to dryness and the residue was recrystallised from IMS to give 3-ethoxy-2-methyl-5-|4-(2-pyridyloxy)anilino|-1,8-naphthyridine dihyrochloride trihydrate. m.p. 244°–247° C. Borderline active (1/1) at 30 mg/kg.

Example 41 a) A mixture of methyl p-nitrophenyl 2,3,4-tri-O-acetyl-β-D-glucouronate (2.0 g), ethanol (70 ml) and platinum oxide catalyst (0.125 g) was hydrogenated with stirring under 3 atmospheres of hydrogen. The mixture was filtered and the filtrate concentrated under reduced pressure to give methyl (p-aminophenyl-2,3,4-tri-O-acetyl-β-D-glucopyranosid)-uronate.

b) Methyl (p-aminophenyl-2,3,4-tri-O-acetyl-β-D-glucopyranosid)uronate (1.5 g) in a small volume of IMS was added to a solution of ethyl 4-chloro-6-ethoxy-7-methyl-1,8-naphthyridine-3-carboxylate (1.05 g) in IMS (40 ml). The mixture was boiled under reflux for 18 hours and then cooled to ambient temperature. The mixture was filtered. The filtrate was diluted with ether and then filtered to give methyl |4-(6-ethoxy-3-ethoxycarbonyl-7-methyl-1,8-naphthyridin-4-ylamino)-phenyl-2,3,4-tri-O-acetyl-β-D-glucopyranosid|uronate hydrochloride hemihydrate, m.p. 200°–204° C.

The following were prepared by analogous methods to those described in these Examples.

Example 42

Ethyl 4-(4-hydroxyanilino)-6-methoxy-1,5-naphthyridine-3-carboxylate hydrochloride, m.p. 205°–207° C. Active (1/1) at 30 mg/kg.

Example 43

4-(6-Methoxy-2-methyl-1,5-naphthyridin-4-ylamino)-2-methylphenol, m.p. 262°–264° C.

Example 44

4-|4-(2-Butoxy)anilino|-6-methoxy-2-methyl-1,5-naphthyridine hydrochloride hydrate, m.p. 151°–153° C. Active (1/2) at 30 mg/kg.

PHARMACEUTICAL EXAMPLES

Example U

In the preparation of capsules, 10 parts by weight of active compound and 240 parts by weight of lactose are de-aggregated and blended. The mixture is filled into hard gelatin capsules, each capsule containing 10 mg active compound.

Example V

Tablets are prepared from the following ingredients.

|  | Parts by Weight |
| --- | --- |
| Active compound | 10 |
| Lactose | 190 |
| Maize starch | 22 |
| Polyvinylpyrrolidone | 10 |
| Magnesium stearate | 3 |

The active compound, the lactose and some of the starch are de-aggregated, blended and the resulting mixture is granulated with a solution of the polyvinylpyrrolidone in ethanol. The dry granulate is blended with magnesium stearate and the rest of the starch. The mixture is then compressed in a tableting machine to give tablets containing 10 mg of active compound.

Example W

Tablets are prepared by the method of the previous Example. The tablets are enteric coated in a conventional manner using a solution of 20% cellulose acetate phthalate and 3% diethyl phthalate in ethanol:dichloromethane (1:1).

Example X

In the preparation of suppositories, 100 parts by weight of active compound is incorporated in 1300 parts by weight of semi-synthetic glycerides as the suppository base and the mixture formed into suppositories each containing 100 mg of active ingredient.

Example Y

In the preparation of capsules, 50 parts by weight of active compound, 300 parts by weight of lactose and 3 parts by weight of magnesium stearate are de-aggregated and blended. The mixture is filled into hard gelatin capsules, each capsule containing 50 mg of active ingredient.

Example Z

The active compound is incorporated into the base by thorough homogenization until the drug is evenly distributed. The ointment is packed into 10 g amber jars with screw-capped lined lids.

| Active compound | 0.1 g |
| --- | --- |
| White soft paraffin to | 10 g |

We claim:
1. Compounds of formula I

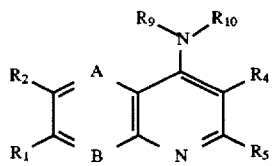

and pharmaceutically acceptable salts thereof in which one of A or B represents N and the other represents C—$R_3$;

$R_1$ represents hydrogen, halo, a $C_{1-6}$ alkyl group, hydroxy, a carboxy $C_{2-4}$ alkenyl group, a $C_{2-6}$ alkoxycarbonyl $C_{2-4}$ alkenyl group, a hydroxy $C_{1-6}$ alkyl group, a carboxy $C_{1-4}$ alkyl group, a $C_{2-6}$ alkoxycarbonyl $C_{1-4}$ alkyl group, a $C_{1-6}$ alkoxy group, a halogenated $C_{1-6}$ alkyl group, a carboxy group, a $C_{2-6}$ alkoxycarbonyl group, a $C_{1-6}$ alkanoylamino group or a carbamoyl $C_{2-4}$ alkenyl group;

$R_2$ represents a $C_{1-6}$ alkoxy group, hydroxy, a $C_{1-6}$ alkanoyloxy group (which may be substituted by a $C_{1-6}$ alkanoyloxy group), or a phenoxy group (optionally substituted by a $C_{1-4}$ alkyl group, halo or a $C_{1-4}$ alkoxy group);

$R_3$ represents hydrogen or a $C_{1-4}$ alkyl group;

$R_4$ represents hydrogen, halo, a $C_{2-7}$ alkoxycarbonyl group, cyano, a benzyloxycarbonyl group (optionally substituted by a $C_{1-4}$ alkyl group, halo or a $C_{1-4}$ alkoxy group), a $C_{1-6}$ alkanoyl group, a benzoyl group (optionally substituted by a $C_{1-4}$ alkyl group, halo or a $C_{1-4}$ alkoxy group), a $C_{1-6}$ alkyl group (optionally substituted by one or more hydroxy groups and or an amino group of formula —$NR_xR_y$ (in which $R_x$ and $R_y$ independently represent hydrogen or a $C_{1-4}$ alkyl group or $R_x$ and $R_y$ together with the nitrogen atom to which they are attached form a pyrrolidine ring, a morpholine ring or a piperidine ring)), a carboxy group, a $C_{1-6}$ alkylthio group or a carbamoyl group of formula —$CONR_aR_b$ (in which $R_a$ and $R_b$ independently represent hydrogen, a $C_{1-6}$ alkyl group (optionally substituted by an amino group of formula —$NR_cR_d$ in which $R_c$ and $R_d$ independently represent hydrogen or a $C_{1-4}$ alkyl group or $R_c$ and $R_d$ together with the nitrogen atom to which they are attached form a pyrrolidine ring, a morpholine ring or a piperidine ring) or $R_a$ and $R_b$ together with the nitrogen atom to which they are attached form a pyrrolidine ring, a morpholine ring or a piperidine ring);

$R_5$ represents hydrogen or a $C_{1-4}$ alkyl group;

$R_9$ represents hydrogen or a $C_{1-4}$ alkyl group;

$R_{10}$ represents a group of formula 1, 2 or 3:

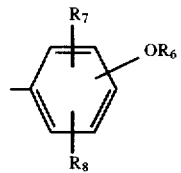

(1)

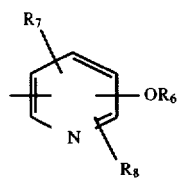

(2)

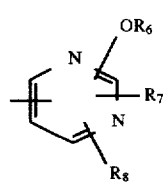

(3)

in which $R_6$ represents hydrogen, a $C_{1-6}$ alkyl group (optionally substituted by one or more of the following: hydroxy, halo, an amino group of formula—$NR_{12}R_{13}$ (in which $R_{12}$ and $R_{13}$ independently represent hydrogen or a $C_{1-4}$ alkyl group or $R_{12}$ and $R_{13}$ together with the nitrogen atom to which they are attached form a pyrrolidine ring, a morpholine ring or a piperidine ring), a $C_{2-7}$ alkoxycarbonyl group or a carbamoyl group of formula $CONR_{14}R_{15}$ (in which $R_{14}$ and $R_{15}$ independently represent hydrogen or a $C_{1-6}$ alkyl group or $R_{14}$ and $R_{15}$ together with the nitrogen to which they are attached form a pyrrolidine ring, a morpholine ring or piperidine ring)); a $C_{3-12}$ alicyclic hydrocarbon group, a phenyl group (optionally substituted by a $C_{1-4}$ alkyl group, halo or a $C_{1-4}$ alkoxy group), a $C_{3-6}$ cycloalkyl $C_{1-4}$ alkyl group or an arylalkyl group (optionally substituted by a $C_{1-4}$ alkyl group, halo or a $C_{1-4}$ alkoxy group); a pyridyl group (optionally substituted by one or more of the following: a $C_{1-4}$ alkyl group, a $C_{1-4}$ alkoxy group, hydroxy or halo);

or when $R_{10}$ represents a group of formula (1) $OR_6$ represents a monosaccharide group or a disaccharide group (optionally derivatised by one or more of the following: oxidation; oxidation followed by esterification; esterification or acetalisation); and $R_7$ and $R_8$ independently represent hydrogen, hydroxy, halo, trifluoromethyl, trifluoromethoxy, a $C_{1-6}$ alkyl group, a carboxy group, a $C_{1-6}$ alkoxy group, or a $C_{2-7}$ alkoxycarbonyl group;

with a first proviso that when $R_1$ represents hydrogen, a $C_{1-6}$ alkyl group, hydroxy, a carboxy $C_{2-4}$ alkenyl group, a $C_{2-6}$ alkoxycarbonyl $C_{2-4}$ alkenyl group, a hydroxy $C_{1-6}$ alkyl group, a carboxy $C_{1-4}$ alkyl group, a $C_{2-6}$ alkoxycarbonyl $C_{1-4}$ alkyl group, a $C_{1-6}$ alkoxy group, a halogenated $C_{1-6}$ alkyl group, a carboxy group, a $C_{2-6}$ alkoxycarbonyl group or a $C_{1-6}$ alkanoylamino group; and $R_2$ represents hydrogen, halo, a $C_{1-6}$ alkoxy group, hydroxy, a $C_{1-6}$ alkanoyloxy group, or a phenoxy group (optionally substituted by a $C_{1-4}$ alkyl group, halo or a $C_{1-4}$ alkoxy group); and $R_4$ represents hydrogen, halo, a $C_{2-7}$ alkoxycarbonyl group, a benzyloxycarbonyl group (optionally substituted by a $C_{1-4}$ alkyl group, halo or a $C_{1-4}$ alkoxy group), a $C_{1-6}$ alkanoyl group, a benzoyl group (optionally substituted by a $C_{1-4}$ alkyl group, halo or a $C_{1-4}$ alkoxy group), carbamoyl, a $C_{1-6}$ alkyl group, a carboxy group, a $C_{1-6}$ hydroxyalkyl group or a $C_{1-6}$ alkylthio group; and $R_5$ represents hydrogen or a $C_{1-4}$ alkyl group; and $R_{10}$ represents a group of formula (1)

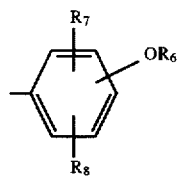

(1)

in which $R_6$ represents hydrogen, a $C_{1-6}$ alkyl group (optionally substituted by one or more of the following: hydroxy, halo or an amino group of formula—$NR_{12}R_{13}$ (in which $R_{12}$ and $R_{13}$ independently represent hydrogen or a $C_{1-4}$ alkyl group or $R_{12}$ and $R_{13}$ together with the nitrogen atom to which they are attached form a pyrrolidine ring, a morpholine ring or a piperidine ring)), a $C_{3-12}$ alicyclic hydrocarbon group, a phenyl group (optionally substituted by a $C_{1-4}$ alkyl group, halo or a $C_{1-4}$ alkoxy group), a $C_{3-6}$ cycloalkyl $C_{1-4}$ alkyl group or a benzyl group (optionally substituted by a $C_{1-4}$ alkyl group, halo or a $C_{1-4}$ alkoxy group); and $R_7$ represents hydrogen, halo, trifluoromethyl, trifluoromethoxy, a $C_{1-6}$ alkyl group, a carboxy group, or a $C_{1-6}$ alkoxy group; and $R_8$ represents hydrogen, halo, trifluoromethyl, trifluoromethoxy, a $C_{1-6}$ alkyl group or a $C_{1-6}$ alkoxy group; and $R_9$ represents hydrogen or a $C_{1-4}$ alkyl group and B represents N then A is other than $CR_3$ in which $R_3$ represents hydrogen or a $C_{1-4}$ alkyl group and a second proviso that when A represents N and B represents CH; $R_1$ represents halo or a halogenated $C_{1-6}$ alkyl group; $R_2$, $R_4$, $R_5$ and $R_9$ each represent hydrogen then $R_{10}$ is other than 4-hydroxyphenyl.

2. Compounds according to claim 1 represented by formula IIa

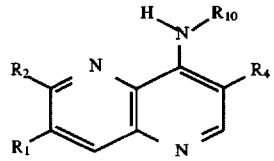

IIa in which $R_1$ represents hydrogen, halo, a $C_{1-6}$ alkyl group, hydroxy, a carboxy $C_{2-4}$ alkenyl group, a $C_{2-6}$ alkoxycarbonyl $C_{2-4}$ alkenyl group, a hydroxy $C_{1-6}$ alkyl group, a carboxy $C_{1-4}$ alkyl group, a $C_{2-6}$ alkoxycarbonyl $C_{1-4}$ alkyl group, a $C_{1-6}$ alkoxy group, a halogenated $C_{1-6}$ alkyl group, a carboxy group, a $C_{2-6}$ alkoxycarbonyl group, a $C_{1-6}$ alkanoylamino group or a carbamoyl $C_{2-4}$ alkenyl group;

$R_2$ represents a $C_{1-6}$ alkoxy group, a $C_{1-6}$ alkyl group, a $C_{1-6}$ alkoxy group, hydroxy, a $C_{1-6}$ alkanoyloxy group (which may be substituted by a $C_{1-6}$ alkanoyloxy group), or a phenoxy group (optionally substituted by a $C_{1-4}$ alkyl group, halo or a $C_{1-4}$ alkoxy group);

$R_4$ represents hydrogen, carbamoyl, a $C_{2-7}$ alkoxycarbonyl group or cyano; and $R_{10}$ represents a group of formula 1, 2 or 3:

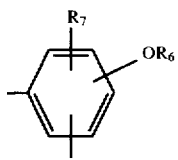  (1)

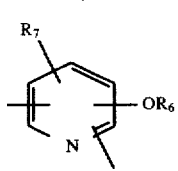  (2)

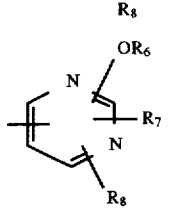  (3)

in which $R_6$ represents hydrogen, a $C_{1-6}$ alkyl group (optionally substituted by one or more of the following: hydroxy, halo, an amino group of formula—$NR_{12}R_{13}$ (in which $R_{12}$ and $R_{13}$ independently represent hydrogen or a $C_{1-4}$ alkyl group or $R_{12}$ and $R_{13}$ together with the nitrogen atom to which they are attached form a pyrrolidine ring, a morpholine ring or a piperidine ring), a $C_{2-7}$ alkoxycarbonyl group or a carbamoyl group of formula $CONR_{14}R_{15}$ (in which $R_{14}$ and $R_{15}$ independently represent hydrogen or a $C_{1-6}$ alkyl group or $R_{14}$ and $R_{15}$ together with the nitrogen atom to which they are attached form a pyrrolidine ring, a morpholine ring or piperidine ring)), a $C_{3-12}$ alicyclic hydrocarbon group, a phenyl group (optionally substituted by a $C_{1-4}$ alkyl group, halo or a $C_{1-4}$ alkoxy group), a $C_{3-6}$ cycloalkyl $C_{1-4}$ alkyl group or an arylalkyl group (optionally substituted by a $C_{1-4}$ alkyl group, halo or a $C_{1-4}$ alkoxy group), or a pyridyl group (optionally substituted by one or more of the following: a $C_{1-4}$ alkyl group, a $C_{1-4}$ alkoxy group, hydroxy or halo);

or when $R_{10}$ represents a group of formula (1) $OR_6$ represents a monosaccharide group or a disaccharide group (optionally derivatised by one or more of the following: oxidation; oxidation followed by esterification; esterification or acetalisation); and $R_7$ and $R_8$ independently represent hydrogen, hydroxy, halo, trifluoromethyl, trifluoromethoxy, a $C_{1-6}$ alkyl group, a carboxy group, a $C_{1-6}$ alkoxy group, or a $C_{2-7}$ alkoxycarbonyl group.

3. Compounds according to claim 2 in which $R_1$ represents hydrogen or chloro;

$R_2$ represents a $C_{1-4}$ alkoxy group or phenoxy;

$R_4$ represents hydrogen or a $C_{2-5}$ alkoxycarbonyl group; and $R_{10}$ represents 4-methoxyphenyl, 4-(2-pyridyloxyphenyl), 2-ethoxy-5-pyridyl, 4-(2-hydroxyethoxy)phenyl, (4-(β-D-galactopyranosyl)phenyl, 4-(2,3-dihydroxypropoxy)phenyl or 3-ethoxycarbonyl-4-hydroxyphenyl.

4. Compounds according to claim 1 represented by formula IIb

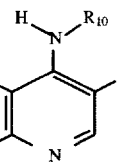  IIb in which $R_1$ represents hydrogen, a $C_{1-4}$ alkyl group, a $C_{1-4}$ alkoxy group or a carbamoyl $C_{2-4}$ alkenyl group;

$R_2$ represents a $C_{1-4}$ alkoxy group or acetoxyacetoxy;

$R_4$ represents hydrogen, a $C_{2-7}$ alkoxycarbonyl group, cyano or carbamoyl; and $R_{10}$ represents a group of formula 1, 2 or 3:

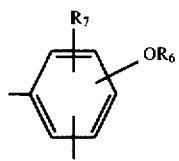  (1)

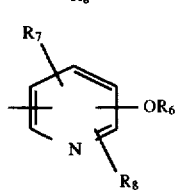  (2)

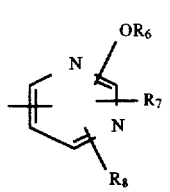  (3)

in which $R_6$ represents hydrogen, a $C_{1-6}$ alkyl group (optionally substituted by one or more of the following: hydroxy, halo, an amino group of formula—$NR_{12}R_{13}$ (in which $R_{12}$ and $R_{13}$ independently represent hydrogen or a $C_{1-4}$ alkyl group or $R_{12}$ and $R_{13}$ together with the nitrogen atom to which they are attached form a pyrrolidine ring, a morpholine ring or a piperidine ring), a $C_{2-7}$ alkoxycarbonyl group or a carbamoyl group of formula $CONR_{14}R_{15}$ (in which $R_{14}$ and $R_{15}$ independently represent hydrogen or a $C_{1-6}$ alkyl group or $R_{14}$ and $R_{15}$ together with the nitrogen to which they are attached form a pyrrolidine ring, a morpholine ring or piperidine ring)); a $C_{3-12}$ alicyclic hydrocarbon group, a phenyl group (optionally substituted by a $C_{1-4}$ alkyl group, halo or a $C_{1-4}$ alkoxy group), a $C_{3-6}$ cycloalkyl $C_{1-4}$ alkyl group or an arylalkyl group (optionally substituted by a $C_{1-4}$ alkyl group, halo or a $C_{1-4}$ alkoxy group); a pyridyl group (optionally substituted by one or more of the following: a $C_{1-4}$ alkyl group, a $C_{1-4}$ alkoxy group, hydroxy or halo);

or when $R_{10}$ represents a group of formula (1) $OR_6$ represents a monosaccharide group or a disaccharide group (optionally derivatised by one or more of the following: oxidation; oxidation followed by esterification; esterification or acetalisation); and $R_7$ and $R_8$ independently represent hydrogen, hydroxy, halo, trifluoromethyl, trifluoromethoxy, a $C_{1-6}$ alkyl group, a carboxy group, a $C_{1-6}$ alkoxy group, or a $C_{2-7}$ alkoxycarbonyl group.

5. Compounds according to claim 4 in which $R_1$ represents hydrogen, a $C_{1-3}$ alkyl group or a $C_{1-3}$ alkoxy group;

$R_2$ represents a $C_{1-4}$ alkoxy group;

$R_4$ represents cyano, carbamoyl or a $C_{2-5}$ alkoxycarbonyl group; and $R_{10}$ represents 4-methoxyphenyl, 6-ethoxy-3-pyridyl, 6-hydroxy-3-pyridyl, 6-ethoxy-2-pyridyl, 4-(carbamoylmethoxy)phenyl, 2,4-dihydroxy-5-pyrimidinyl, 2-(pyrid-3-yloxy)pyrid-5-yl, 2-phenoxy-5-pyridyl, 4-(ethoxycarbonylmethoxy)phenyl, 3-ethoxy-carbonyl-4-hydroxyphenyl, 4-(2-pyridyloxy)phenyl, 4-(β-D-lactopyranosyl)phenyl or 4-(β-D-galactopyranosyl)phenyl.

6. Compounds according to claim 1 represented by formula IIc

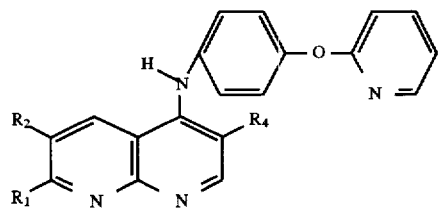

IIc in which $R_1$ represents hydrogen, a $C_{1-4}$ alkyl group or a $C_{1-4}$ alkoxy group;

$R_2$ represents hydrogen or $C_{1-4}$ alkoxy group; and $R_4$ represents hydrogen or a $C_{2-5}$ alkoxycarbonyl group.

7. Compounds according to claim 6 in which $R_1$ represents hydrogen or a $C_{1-4}$ alkyl group;

$R_2$ represents hydrogen, methoxy, ethoxy or propoxy; and $R_4$ represents hydrogen, methoxycarbonyl, ethoxycarbonyl or propoxycarbonyl.

8. Compounds represented by formula IId

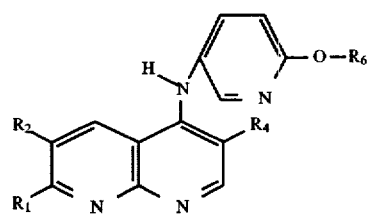

IId in which $R_1$ represents hydrogen, a $C_{1-4}$ alkyl group or a $C_{1-4}$ alkoxy group;

$R_2$ represents a $C_{1-4}$ alkoxy group;

$R_4$ represents hydrogen or a $C_{2-5}$ alkoxycarbonyl group and $R_6$ represents hydrogen or a $C_{1-4}$ alkyl group.

9. Compounds according to claim 8 in which $R_1$ represents hydrogen, methyl, ethyl or ethoxy;

$R_2$ represents methoxy, ethoxy or propoxy;

$R_4$ represents hydrogen, methoxycarbonyl, ethoxycarbonyl or propoxycarbonyl; and $R_6$ represents hydrogen, methyl, ethyl or propyl.

10. A compound selected from
ethyl 6-ethoxy-4-(4-methoxyanilino)-1,5-naphthyridine-3-carboxylate;
ethyl 6-ethoxy-4-|4-(2-hydroxyethoxy)anilino|-1,5-naphthyridine-3-carboxylate;
ethyl 6-ethoxy-4-|4-(β-D-galactopyranosyl)anilino|-1,5-naphthyridine-3-carboxylate;
ethyl 7-(2-carbamoylvinyl)-6-ethoxy-4-(4-methoxyanilino)-1,8-naphthyridine-3-carboxylate;
ethyl 7-ethoxy-4-(2-ethoxy-5-pyridylamino)-1,8-naphthyridine-3-carboxylate;
ethyl 7-methyl-4|4-(2-pyridyloxy)-anilino|-1,8-naphthyridine-3-carboxylate;
and pharmaceutically acceptable salts thereof.

11. A pharmaceutical composition comprising a therapeutically effective amount of a compound of formula I

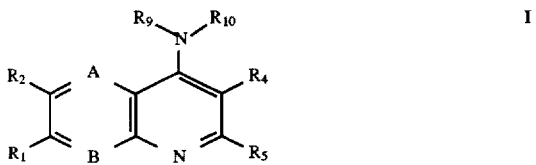

I and pharmaceutically acceptable salts thereof in which one of A or B represents N and the other represents N or C—$R_3$;

$R_1$ represents hydrogen, halo, a $C_{1-6}$ alkyl group, hydroxy, a carboxy $C_{2-4}$ alkenyl group, a $C_{2-6}$ alkoxycarbonyl $C_{2-4}$ alkenyl group, a hydroxy $C_{1-6}$ alkyl group, a carboxy $C_{1-4}$ alkyl group, a $C_{2-6}$ alkoxycarbonyl $C_{1-4}$ alkyl group, a $C_{1-6}$ alkoxy group, a halogenated $C_{1-6}$ alkyl group, a carboxy group, a $C_{2-6}$ alkoxycarbonyl group, a $C_{1-6}$ alkanoylamino group or a carbamoyl $C_{2-4}$ alkenyl group;

$R_2$ represents hydrogen, a $C_{1-6}$ alkyl group, halo, a $C_{1-6}$ alkoxy group, hydroxy, a $C_{1-6}$ alkanoyloxy group (which may be substituted by a $C_{1-6}$ alkanoyloxy group), or a phenoxy group (optionally substituted by a $C_{1-4}$ alkyl group, halo or a $C_{1-4}$ alkoxy group);

$R_3$ represents hydrogen or a $C_{1-4}$ alkyl group;

$R_4$ represents hydrogen, halo, a $C_{2-7}$ alkoxycarbonyl group, cyano, a benzyloxycarbonyl group (optionally substituted by a $C_{1-4}$ alkyl group, halo or a $C_{1-4}$ alkoxy group), a $C_{1-6}$ alkanoyl group, a benzoyl group (optionally substituted by a $C_{1-4}$ alkyl group, halo or a $C_{1-4}$ alkoxy group), a $C_{1-6}$ alkyl group (optionally substituted by one or more hydroxy groups and or an amino group of formula —$NR_xR_y$ (in which $R_x$ and $R_y$ independently represent hydrogen or a $C_{1-4}$ alkyl group or $R_x$ and $R_y$ together with the nitrogen atom to which they are attached form a pyrrolidine ring, a morpholine ring or a piperidine ring)), a carboxy group, a $C_{1-6}$ alkylthio group or a carbamoyl group of formula —$CONR_aR_b$ (in which $R_a$ and $R_b$ independently represent hydrogen, a $C_{1-6}$ alkyl group (optionally substituted by an amino group of formula —$NR_cR_d$ in which $R_c$ and $R_d$ independently represent hydrogen or a $C_{1-4}$ alkyl group or $R_c$ and $R_d$ together with the nitrogen atom to which they are attached form a pyrrolidine ring, a morpholine ring or a piperidine ring) or $R_a$ and $R_b$ together with the nitrogen atom to which they are attached form a pyrrolidine ring, a morpholine ring or a piperidine ring);

$R_5$ represents hydrogen or a $C_{1-4}$ alkyl group;

$R_9$ represents hydrogen or a $C_{1-4}$ alkyl group;

41

$R_{10}$ represents a group of formula 1, 2 or 3:

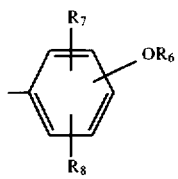

(1)

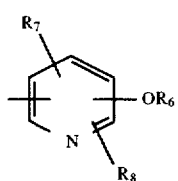

(2)

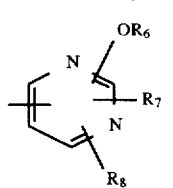

(3)

in which $R_6$ represents hydrogen, a $C_{1-6}$ alkyl group (optionally substituted by one or more of the following: hydroxy, halo, an amino group of formula—$NR_{12}R_{13}$ (in which $R_{12}$ and $R_{13}$ independently represent hydrogen or a $C_{1-4}$ alkyl group or $R_{12}$ and $R_{13}$ together with the nitrogen atom to which they are attached form a pyrrolidine ring, a morpholine ring or a piperidine ring), a $C_{2-7}$ alkoxycarbonyl group or a carbamoyl group of formula $CONR_{14}R_{15}$ (in which $R_{14}$ and $R_{15}$ independently represent hydrogen or a $C_{1-6}$ alkyl group or $R_{14}$ and $R_{15}$ together with the nitrogen to which they are attached form a pyrrolidine ring, a morpholine ring or piperidine ring)); a $C_{3-12}$ alicyclic hydrocarbon group, a phenyl group (optionally substituted by a $C_{1-4}$ alkyl group, halo or a $C_{1-4}$ alkoxy group), a $C_{3-6}$ cycloalkyl $C_{1-4}$ alkyl group or an arylalkyl group (optionally substituted by a $C_{1-4}$ alkyl group, halo or a $C_{1-4}$ alkoxy group); a pyridyl group (optionally substituted by one or more of the following: a $C_{1-4}$ alkyl group, a $C_{1-4}$ alkoxy group, hydroxy or halo);

or when $R_{10}$ represents a group of formula (1) $OR_6$ represents a monosaccharide group or a disaccharide group (optionally derivatised by one or more of the following: oxidation; oxidation followed by esterification; esterification or acetalisation); and $R_7$ and $R_8$ independently represent hydrogen, hydroxy, halo, trifluoromethyl, trifluoromethoxy, a $C_{1-6}$ alkyl group, a carboxy group, a $C_{1-6}$ alkoxy group, or a $C_{2-7}$ alkoxycarbonyl group;

with the proviso that when $R_1$ represents hydrogen, a $C_{1-6}$ alkyl group, hydroxy, a carboxy $C_{2-4}$ alkenyl group, a $C_{2-6}$ alkoxycarbonyl $C_{2-4}$ alkenyl group, a hydroxy $C_{1-6}$ alkyl group, a carboxy $C_{1-4}$ alkyl group, a $C_{2-6}$ alkoxycarbonyl $C_{1-4}$ alkyl group, a $C_{1-6}$ alkoxy group, a halogenated $C_{1-6}$ alkyl group, a carboxy group, a $C_{2-6}$ alkoxycarbonyl group or a $C_{1-6}$ alkanoylamino group; and $R_2$ represents hydrogen, halo, a $C_{1-6}$ alkoxy group, hydroxy, a $C_{1-6}$ alkanoyloxy group, or a phenoxy group (optionally substituted by a $C_{1-4}$ alkyl group, halo or a $C_{1-4}$ alkoxy group); and $R_4$ represents hydrogen, halo, a $C_{2-7}$ alkoxycarbonyl group, a benzyloxycarbonyl group (optionally substi-

42 tuted by a $C_{1-4}$ alkyl group, halo or a $C_{1-4}$ alkoxy group), a $C_{1-6}$ alkanoyl group, a benzoyl group (optionally substituted by a $C_{1-4}$ alkyl group, halo or a $C_{1-4}$ alkoxy group), carbamoyl, a $C_{1-6}$ alkyl group, a carboxy group, a $C_{1-6}$ hydroxyalkyl group or a $C_{1-6}$ alkylthio group; and $R_5$ represents hydrogen or a $C_{1-4}$ alkyl group; and $R_{10}$ represents a group of formula (1)

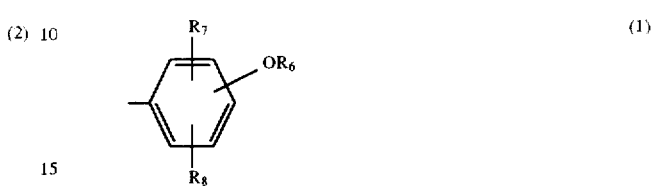

(1)

in which $R_6$ represents hydrogen, a $C_{1-6}$ alkyl group (optionally substituted by one or more of the following: hydroxy, halo or an amino group of formula—$NR_{12}R_{13}$ (in which $R_{12}$ and $R_{13}$ independently represent hydrogen or a $C_{1-4}$ alkyl group or $R_{12}$ and $R_{13}$ together with the nitrogen atom to which they are attached form a pyrrolidine ring, a morpholine ring or a piperidine ring)), a $C_{3-12}$ alicyclic hydrocarbon group, a phenyl group (optionally substituted by a $C_{1-4}$ alkyl group, halo or a $C_{1-4}$ alkoxy group), a $C_{3-6}$ cycloalkyl $C_{1-4}$ alkyl group or a benzyl group (optionally substituted by a $C_{1-4}$ alkyl group, halo or a $C_{1-4}$ alkoxy group); and $R_7$ represents hydrogen, halo, trifluoromethyl, trifluoromethoxy, a $C_{1-6}$ alkyl group, a carboxy group, or a $C_{1-6}$ alkoxy group; and $R_8$ represents hydrogen, halo, trifluoromethyl, trifluoromethoxy, a $C_{1-6}$ alkyl group or a $C_{1-6}$ alkoxy group; and $R_9$ represents hydrogen or a $C_{1-4}$ alkyl group and B represents N then A is other than $CR_3$ in which $R_3$ represents hydrogen or a $C_{1-4}$ alkyl group;

together with a pharmaceutically acceptable diluent or carrier.

12. A method of treating rheumatic diseases, comprising the administration of a therapeutically effective amount of a compound of formula I

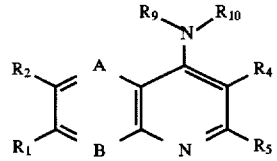

I and pharmaceutically acceptable salts thereof in which one of A or B represents N and the other represents C—$R_3$;

$R_1$ represents hydrogen, halo, a $C_{1-6}$ alkyl group, hydroxy, a carboxy $C_{2-4}$ alkenyl group, a $C_{2-6}$ alkoxycarbonyl $C_{2-4}$ alkenyl group, a hydroxy $C_{1-6}$ alkyl group, a carboxy $C_{1-4}$ alkyl group, a $C_{2-6}$ alkoxycarbonyl $C_{1-4}$ alkyl group, a $C_{1-6}$ alkoxy group, a halogenated $C_{1-6}$ alkyl group, a carboxy group, a $C_{2-6}$ alkoxycarbonyl group, a $C_{1-6}$ alkanoylamino group or a carbamoyl $C_{2-4}$ alkenyl group;

$R_2$ represents hydrogen, a $C_{1-6}$ alkyl group, halo, a $C_{1-6}$ alkoxy group, hydroxy, a $C_{1-6}$ alkanoyloxy group (which may be substituted by a $C_{1-6}$ alkanoyloxy group), or a phenoxy group (optionally substituted by a $C_{1-4}$ alkyl group, halo or a $C_{1-4}$ alkoxy group);

R₃ represents hydrogen or a $C_{1-4}$ alkyl group;

R₄ represents hydrogen, halo, a $C_{2-7}$ alkoxycarbonyl group, cyano, a benzyloxycarbonyl group (optionally substituted by a $C_{1-4}$ alkyl group, halo or a $C_{1-4}$ alkoxy group), a $C_{1-6}$ alkanoyl group, a benzoyl group (optionally substituted by a $C_{1-4}$ alkyl group, halo or a $C_{1-4}$ alkoxy group), a $C_{1-6}$ alkyl group (optionally substituted by one or more hydroxy groups and or an amino group of formula —NR$_x$R$_y$ (in which R$_x$ and R$_y$ independently represent hydrogen or a $C_{1-4}$ alkyl group or R$_x$ and R$_y$ together with the nitrogen atom to which they are attached form a pyrrolidine ring, a morpholine ring or a piperidine ring)), a carboxy group, a $C_{1-6}$ alkylthio group or a carbamoyl group of formula —CONR$_a$R$_b$ (in which R$_a$ and R$_b$ independently represent hydrogen, a $C_{1-6}$ alkyl group (optionally substituted by an amino group of formula —NR$_c$R$_d$ in which R$_c$ and R$_d$ independently represent hydrogen or a $C_{1-4}$ alkyl group or R$_c$ and R$_d$ together with the nitrogen atom to which they are attached form a pyrrolidine ring, a morpholine ring or a piperidine ring) or R$_a$ and R$_b$ together with the nitrogen atom to which they are attached form a pyrrolidine ring, a morpholine ring or a piperidine ring);

R₅ represents hydrogen or a $C_{1-4}$ alkyl group;

R₉ represents hydrogen or a $C_{1-4}$ alkyl group;

R₁₀ represents a group of formula 1, 2 or 3:

in which

R₆ represents hydrogen, a $C_{1-6}$ alkyl group (optionally substituted by one or more of the following: hydroxy,

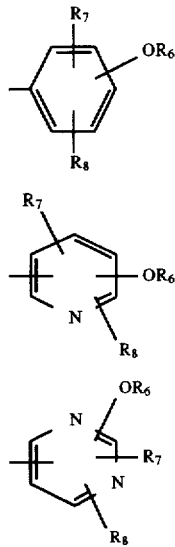

halo, an amino group of formula—NR₁₂R₁₃ (in which R₁₂ and R₁₃ independently represent hydrogen or a $C_{1-4}$ alkyl group or R₁₂ and R₁₃ together with the nitrogen atom to which they are attached form a pyrrolidine ring, a morpholine ring or a piperidine ring), a $C_{2-7}$ alkoxycarbonyl group or a carbamoyl group of formula CONR₁₄R₁₅ (in which R₁₄ and R₁₅ independently represent hydrogen or a $C_{1-6}$ alkyl group or R₁₄ and R₁₅ together with the nitrogen to which they are attached form a pyrrolidine ring, a morpholine ring or piperidine ring)); a $C_{3-12}$ alicyclic hydrocarbon group, a phenyl group (optionally substituted by a $C_{1-4}$ alkyl group, halo or a $C_{1-4}$ alkoxy group), a $C_{3-6}$ cycloalkyl $C_{1-4}$ alkyl group or an arylalkyl group (optionally substituted by a $C_{1-4}$ alkyl group, halo or a $C_{1-4}$ alkoxy group); a pyridyl group (optionally substituted by one or more of the following: a $C_{1-4}$ alkyl group, a $C_{1-4}$ alkoxy group, hydroxy or halo);

or when R₁₀ represents a group of formula (1) OR₆ represents a monosaccharide group or a disaccharide group (optionally derivatised by one or more of the following: oxidation; oxidation followed by esterification; esterification or acetalisation); and R₇ and R₈ independently represent hydrogen, hydroxy, halo, trifluoromethyl, trifluoromethoxy, a $C_{1-6}$ alkyl group, a carboxy group, a $C_{1-6}$ alkoxy group, or a $C_{2-7}$ alkoxycarbonyl group;

with the proviso that when

R₁ represents hydrogen, a $C_{1-6}$ alkyl group, hydroxy, a carboxy $C_{2-4}$ alkenyl group, a $C_{2-6}$ alkoxycarbonyl $C_{2-4}$ alkenyl group, a hydroxy $C_{1-6}$ alkyl group, a carboxy $C_{1-4}$ alkyl group, a $C_{2-6}$ alkoxycarbonyl $C_{1-4}$ alkyl group, a $C_{1-6}$ alkoxy group, a halogenated $C_{1-6}$ alkyl group, a carboxy group, a $C_{2-6}$ alkoxycarbonyl group or a $C_{1-6}$ alkanoylamino group; and R₂ represents hydrogen, halo, a $C_{1-6}$ alkoxy group, hydroxy, a $C_{1-6}$ alkanoyloxy group, or a phenoxy group (optionally substituted by a $C_{1-4}$ alkyl group, halo or a $C_{1-4}$ alkoxy group); and R₄ represents hydrogen, halo, a $C_{2-7}$ alkoxycarbonyl group, a benzyloxycarbonyl group (optionally substituted by a $C_{1-4}$ alkyl group, halo or a $C_{1-4}$ alkoxy group), a $C_{1-6}$ alkanoyl group, a benzoyl group (optionally substituted by a $C_{1-4}$ alkyl group, halo or a $C_{1-4}$ alkoxy group), carbamoyl, a $C_{1-6}$ alkyl group, a carboxy group, a $C_{1-6}$ hydroxyalkyl group or a $C_{1-6}$ alkylthio group; and R₅ represents hydrogen or a $C_{1-4}$ alkyl group; and R₁₀ represents a group of formula (1)

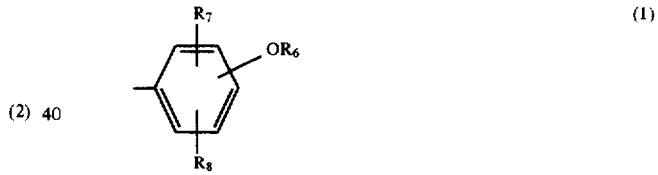

in which

R₆ represents hydrogen, a $C_{1-6}$ alkyl group (optionally substituted by one or more of the following: hydroxy, halo or an amino group of formula—NR₁₂R₁₃ (in which R₁₂ and R₁₃ independently represent hydrogen or a $C_{1-4}$ alkyl group or R₁₂ and R₁₃ together with the nitrogen atom to which they are attached form a pyrrolidine ring, a morpholine ring or a piperidine ring)), a $C_{3-12}$ alicyclic hydrocarbon group, a phenyl group (optionally substituted by a $C_{1-4}$ alkyl group, halo or a $C_{1-4}$ alkoxy group), a $C_{3-6}$ cycloalkyl $C_{1-4}$ alkyl group or a benzyl group (optionally substituted by a $C_{1-4}$ alkyl group, halo or a $C_{1-4}$ alkoxy group); and R₇ represents hydrogen, halo, trifluoromethyl, trifluoromethoxy, a $C_{1-6}$ alkyl group, a carboxy group, or a $C_{1-6}$ alkoxy group; and R₈ represents hydrogen, halo, trifluoromethyl, trifluoromethoxy, a $C_{1-6}$ alkyl group or a $C_{1-6}$ alkoxy group; and R₉ represents hydrogen or a $C_{1-4}$ alkyl group and B represents N then A is other than CR₃ in which R₃ represents hydrogen or a $C_{1-4}$ alkyl group;

to a mammal in need thereof.

13. A process to prepare a compound of formula I

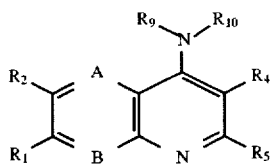

as defined in claim 1, comprising:

a) reacting a compound of formula III

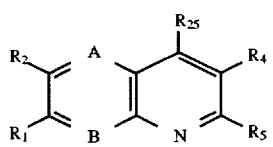

in which $R_{25}$ represents a leaving group with a compound of formula IV

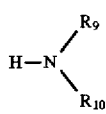

or a salt thereof by heating, optionally in the presence of an inert organic liquid which is preferably a solvent for the reactants, at a temperature in the range 0°–150° C., preferably in the range 30°–120° C., at atmospheric pressure, optionally in the presence of an acid, or a base; or b) reacting a compound of formula XVII

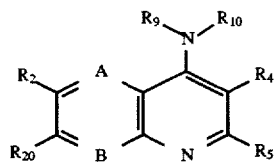

in which $R_{20}$ represents a leaving group with an alkali metal $C_{1-6}$ alkoxide, by heating optionally in the presence of an inert organic liquid which is preferably a solvent for the reactants, at a temperature in the range 50°–250° C. preferably 150°–200° C. preferably in a sealed vessel under pressure, to give a compound of formula I in which $R_1$ represents a $C_{16}$ alkoxy group; or c) displacing $R_{20}$ from a compound of formula XVII, in which $R_{20}$ represents a leaving group, by reaction with an alkali metal hydroxide in the presence of an inert organic liquid or by hydrolysis using an aqueous acid or base, at a temperature in the range 0°–200° C. to give a compound of formula I in which $R_{20}$ represents hydroxy.

14. A compound selected from the group consisting of
ethyl 6-ethoxy-4-(4-(2-diethylaminoethoxy)anilino)-1,5-naphthyridine-3-carboxylate;
ethyl 6-methoxy-4-(4-methoxyanilino)-1,5-naphthyridine-3-carboxylate;
ethyl 6-ethoxy-4-(4-(2-pyridyloxy)anilino)-1,5-naphthyridine-3-carboxylate;
ethyl 6-ethoxy-4-(2-ethoxy-5-pyridylamino)-1,5-naphthyridine-3-carboxylate;
ethyl 4-(4-methoxyanilino)-6-phenoxy-1,5-naphthyridine-3-carboxylate hydrochloride;
ethyl 6-ethyl-4-(4-methoxyanilino)-1,5-naphthyridine3-carboxylate;
ethyl 6-ethoxy-4-(4-(2,3-dihydroxypropoxy)anilino)-1,5-naphthyridine-3-carboxylate;
ethyl 5-(6-ethoxy-3-ethoxycarbonyl-1,5-naphthyridin-4-ylamino) salicylate;
5-(4-methoxyanilino)-2-methyl-1,8-naphthyridin-3-yl acetoxyacetate;
ethyl 6-ethoxy-4-(2-ethoxy-5-pyridylamino)-7-methyl-1,8-naphthyridine-3-carboxylate;
5-(3-ethoxy-2-methyl-1,8-naphthyridin-5-ylamino)pyridin-2-ol;
3-ethoxy-5-(2-ethoxy-5-pyridylamino)-2-methyl-1,8-naphthyridine;
3-ethoxy-5-(6-ethoxy-2-pyridylamino)-2-methyl-1,8-naphthyridine;
ethyl 6-ethoxy-4-(6-ethoxy-2-pyridylamino)-7-methyl-1,8-naphthyridine-3-carboxylate;
6-ethoxy-4-(4-methoxyanilino)-7-methyl-1,8-naphthyridine-3-carbonitrile;
ethyl 4-(4-(carbamoylmethoxy)anilino)-6-ethoxy-7-methyl-1,8-naphthyridine-3-carboxylate;
ethyl 4-(2,4-dihydroxy-5-pyrimidinylamino)-6-ethoxy-7-methyl-1,8-naphthyridine-3-carboxylate;
2-methyl-5-(2-(pyrid-3-yloxy)pyrid-5-ylamino)-1,8-naphthyridine;
ethyl 6-ethoxy-7-methyl-4-(2-phenoxy-5-pyridylamino)-1,8-naphthyridine-3-carboxylate;
ethyl 4-(6-ethoxy-3-ethoxycarbonyl-7-methyl-1,8-naphthyridin-4-ylamino)phenoxyacetate;
ethyl 5-(6-ethoxy-3-ethoxycarbonyl-7-methyl-1,8-naphthyridin-4-ylamino)salicylate;
3-O-(4-(6-ethoxy-3-ethoxycarbonyl-7-methyl-1,8-naphthyridin-4-ylamino)phenyl)-1,2-O-isopropylidene-glucofuranose;
ethyl 6-ethoxy-4-(4-(β-D-galactopyranosyl)anilino)-7-methyl-1,8-naphthyridine-3-carboxylate;
4-(6-ethoxy-7-methyl-1,8-naphthyridin-4-ylamino)phenyl β-D-galactopyranoside;
3-O-(4-(6-ethoxy-7-methyl-1,8-naphthyridin-4-ylamino) phenyl)-1,2:5,6-di-O-isopropylidene-D-glucofuranose;
ethyl 6-ethoxy-4-(4-(β-D-lactopyranosyl)anilino)-7-methyl-1,8-naphthyridine-3-carboxylate;
6-ethoxy-4-(4-(β-D-lactopyranosyl)anilino)-7-methyl-1,8-naphthyridine-3-carboxamide;
ethyl 4-(4-(β-D-galactopyranosyl)anilino)-7-methyl-6-propoxy-1,8-naphthyridine-3-carboxylate;
2-methyl-5-(4-(2-pyridyloxy)anilino)-1,8-naphthyridine;
ethyl 6-ethoxy-7-methyl-4-(4-(2-pyridyloxy)anilino)-1,8-naphthyridine-3-carboxylate;
3-ethoxy-2-methyl-5-(4-(2-pyridyloxy)anilino)-1,8-naphthyridine;
methyl (4-(6-ethoxy-3-ethoxycarbonyl-7-methyl-1,8-naphthyridin-4-ylamino)phenyl-2,3,4-tri-O-acetyl-β-D-glucopyranosid)uronate;
ethyl 4-(4-hydroxyanilino)-6-methoxy-1,5-naphthyridine-3-carboxylate;
4-(6-methoxy-2-methyl-1,5-naphthyridin-4-ylamino)-2-methylphenol; and
4-(4-(2-butoxy)anilino)-6-methoxy-2-methyl-1,5-naphthyridine;

and pharmaceutically acceptable salts thereof.

* * * * *